United States Patent
Swanson et al.

(10) Patent No.: US 10,809,750 B2
(45) Date of Patent: Oct. 20, 2020

(54) OPTICAL PROBE

(71) Applicants: Eric Swanson, Gloucester, MA (US); OFS Fitel, LLC, Norcross, GA (US)

(72) Inventors: Eric Swanson, Gloucester, MA (US); Tristan Kremp, Somerset, NJ (US); Paul S. Westbrook, Basking Ridge, NJ (US); David DiGiovanni, Mountain Lakes, NJ (US)

(73) Assignees: Eric Swanson, Gloucester, MA (US); OFS Fitel, LLC, Norcross, GA (US)

( * ) Notice: Subject to any disclaimer, the term of this patent is extended or adjusted under 35 U.S.C. 154(b) by 0 days.

(21) Appl. No.: 16/524,135

(22) Filed: Jul. 28, 2019

(65) Prior Publication Data

US 2019/0369650 A1 Dec. 5, 2019

Related U.S. Application Data

(63) Continuation of application No. 15/868,521, filed on Jan. 11, 2018, now Pat. No. 10,401,883.

(51) Int. Cl.
*G01J 3/00* (2006.01)
*G05D 25/02* (2006.01)
(Continued)

(52) U.S. Cl.
CPC .............. *G05D 25/02* (2013.01); *A61B 1/06* (2013.01); *A61B 1/07* (2013.01); *G01J 3/44* (2013.01);
(Continued)

(58) Field of Classification Search
CPC ....... G01J 3/00; G01J 3/02; G01J 3/44; G02B 6/04; G02B 6/26; G02B 27/00;
(Continued)

(56) References Cited

U.S. PATENT DOCUMENTS

| 5,152,748 A | 10/1992 | Chastagner |
| 6,485,413 B1 | 11/2002 | Boppart et al. |

(Continued)

FOREIGN PATENT DOCUMENTS

| EP | 0981733 B1 | 11/2004 |
| EP | 0883793 B1 | 11/2007 |

(Continued)

OTHER PUBLICATIONS

Amir Porat, Ori Katz, Esben Ravn Andresen, Herve Rigneault, Dan Oron, Sylvain Gigan, "Widefield Lensless Endoscopy via Speckle Correlations", Optics and Photonics News, Dec. 2016, p. 41.

(Continued)

*Primary Examiner* — Abdullahi Nur
(74) *Attorney, Agent, or Firm* — Kurt Rauschenbach; Rauschenbach Patent Law Group, PLLC

(57) ABSTRACT

An optical probe includes an optical source that generates an optical beam that propagates from a proximal end to a distal end of an optical fiber that imparts a transformation of a spatial profile of the optical beam. An optical control device imparts a compensating spatial profile on the optical beam that at least partially compensates for the transformation of the spatial profile of the optical beam imparted by the optical fiber in response to a control signal from a signal processor. A distal optical source generates a calibration light that propagates through the one or more optical waveguides from the distal end to the proximal end of the optical fiber. An optical detector detects the calibration light and generates electrical signals in response to the detected calibration light. The signal processor generates the control signal to instruct the optical control device to impart the compensating spatial profile on the optical beam that at least partially compensates for the transformation of the spatial profile of the optical beam imparted by the optical fiber.

20 Claims, 16 Drawing Sheets

(51) Int. Cl.
G01J 3/44 (2006.01)
A61B 1/06 (2006.01)
G02B 6/04 (2006.01)
A61B 1/07 (2006.01)
G01J 3/02 (2006.01)

(52) U.S. Cl.
CPC ............. *G01J 3/4406* (2013.01); *G02B 6/04* (2013.01); *G01J 3/0218* (2013.01)

(58) Field of Classification Search
CPC .......... G02B 27/48; G02F 1/01; G05D 25/02; A61B 1/06; A61B 8/00; A61B 8/08; A61B 8/12; A61B 5/00; G10K 15/04
See application file for complete search history.

(56) References Cited

U.S. PATENT DOCUMENTS

| | | | |
|---|---|---|---|
| 7,843,572 | B2 | 11/2010 | Tearney et al. |
| 9,464,883 | B2 | 10/2016 | Swanson et al. |
| 9,683,928 | B2 | 6/2017 | Swanson |
| 10,107,616 | B2 | 10/2018 | Zhou |
| 10,132,610 | B2 | 11/2018 | Swanson et al. |
| 10,401,883 | B2* | 9/2019 | Swanson |
| 10,416,288 | B2 | 9/2019 | Swanson |
| 2010/0253949 | A1* | 10/2010 | Adler ............... A61B 5/0066 356/479 |
| 2011/0218404 | A1 | 9/2011 | Hirakawa |
| 2012/0099112 | A1 | 4/2012 | Alphonse et al. |
| 2012/0226118 | A1 | 9/2012 | Delbeke et al. |
| 2014/0160488 | A1 | 6/2014 | Zhou |
| 2014/0235948 | A1 | 8/2014 | Mahalati et al. |
| 2015/0015879 | A1 | 1/2015 | Papadopoulos et al. |
| 2017/0017075 | A1* | 1/2017 | Reddy ............... G01B 11/2513 |
| 2017/0143196 | A1 | 5/2017 | Liang et al. |
| 2017/0205253 | A1 | 7/2017 | Handerek |

FOREIGN PATENT DOCUMENTS

| | | |
|---|---|---|
| EP | 2333990 A1 | 6/2011 |
| EP | 1839375 B1 | 6/2014 |
| WO | 2016207881 A1 | 12/2016 |

OTHER PUBLICATIONS

Martin Ploschner, Tomas Tyc and Tomas Ciamar, "Seeing through chaos in multimode fibres", Nature Photonics, doi: 10:1038/NPHOTON.2015, Jul. 2015,112, pp. 529-538.
Tomas Cizmár and Kishan Dholakia, "Exploiting multimode waveguides for pure fibre-based imaging" Nature Communications, 3:1027, doi: 10.1038/ncomms2024, May 2012.
Martin Ploschner, Branislav Straka, Kishan Dholakia and Tomas Cizmar, "Fibre-based imaging: new challenges", Adaptive Optics and Wavefront Control for Biological Systems, Proc. of SPIE vol. 9335, 93350H, doi: 10.1117/12.2077693, Mar. 2015.
M. Ploschner, B. Straka, K. Dholakia, and T. Cizmar, "GPU accelerated toolbox for real-time beam-shaping in multimode fibres", Optics Express, 2014, vol. 22, No. 3, doi:10.1364/OE.22.002933.
Miguel A. Preciado, Michael Mazilu, Kishan Dholakia, "Multi-mode fibre correction for applications in optomechanics using a digital micromirror device", FTu1A.6, FiO/LS, OSA 2014.
Miguel A. Preciado, Kishan Dholakia, Michael Mazilu, "Real-time optical eigenmode characterization", FTh3G.5, FiO/LS, OSA 2014.
Reza Nasiri, Mahalati, Ruo, Yu Gu, and Joseph M. Kahn, "Resolution limits for imaging through multi-mode fiber", Optics Express, Jan. 2013, vol. 21, No. 1.
S. G. Adie, N. D. Shemonski, T. S. Ralston, P. S. Carney, S. A. Boppart, "Interferometric Synthetic Aperture Microscopy (ISAM)", In Optical Coherence Tomography: Technology and Applications. 2nd ed.; Drexler, W., Fujimoto, J. G., Eds.; Springer International Publishing, Switzerland, 2015, 965-1004, 2015.

Y. Xu, Y. Z. Liu, S. k Boppart, P. S. Carney, "Automated Interferometric Synthetic Aperture Microscopy and Computational Adaptive Optics for Improved Optical Coherence Tomography", Applied Optics, 55, (8), 2034-2041, doi:10.1364/Ao.55.002034, 2016.
F. A. South, Y. Z. Liu, Y. Xu, N. D. Shemonski, P. S. Carney, S. A. Boppart, "Polarization-Sensitive Interferometric Synthetic Aperture Microscopy", Applied Physics Letters, 107, (21), DOI: Artn 211106 10.1063/1.4936236, 2015.
Aleksandar Lukic, Sebastian Dochow, Hyeonsoo Bae, Gregor Matz, Ines Latka, Bernhard Messerschmidt, Michael Schmitt, and Jürgen Popp, "Endoscopic fiber probe for nonlinear spectroscopic imaging", Optica, vol. 4, No. 5, doi: 10.1364/OPTICA.4.000496, 2017.
Ruo Yu Gu, Reza Nasiri Mahalati, and Joseph M. Kahn, "Design of flexible multi-mode fiber endoscope", Optics Express, Oct. 2015,vol. 23, No. 21, doi:10.1364/OE.23.026905.
C. Bellanger, A. Brignon, J. Colineau, and J. P. Huignard, "Coherent fiber combining by digital holography", Optics Letters, Dec. 2008, vol. 33, No. 24.
Tomas Cizmar, "Exploiting multimode waveguides for in vivo imaging" SPIE Newsroom, http://www.spie.org/newsroom/6106-exploiting-multimode-waveguides-for-in-vivo-imaging, Sep. 2015.
Yuan-Zhi Liu, F. A. South, Y. Xu, P. S. Carney, and S. A. Boppart, "Computational optical coherence tomography", https://doi.org/10.1364/BOE.8.001549, Feb. 2017.
David B. Cole, Cheryl Sorace-Agaskar, Michele Moresco, Gerald Leake, Douglas Goolbaugh, and Michel R. Watts, "Integrated heterodyne interferometer with on-chip modulators and detectors", Optics Letters, vol. 40, No. 13, Jul. 1, 2015.
Chao Zuo, Jiasong Sun, Jiaji Li, Qian Chen, "Computational microscopy with programmable illumination and coded aperture", Proceedings of the SPIE, vol. 10250, doi: 10.1117/12.2266652, 2016.
Ioannis N. Papadopoulos, Salma Farahi, Christophe Moser, and Demetri Psaltis, "High-resolution, lensless endoscope based on digital scanning through a multimode optical fiber", Biomedical Optics Express, V. 4, No. 3. 2013.
Jason P. Moore and Matthew D. Rogge, "Shape sensing using multi-core fiber optic cable and parametric curve solutions", Optics Express, vol. 20, Issue 3, pp. 2967-2973, https://doi.org/10.1364/OE.20.002967, 2012.
Paul S. Westbrook, Tristan Kremp, Kenneth S. Feder, Wing Ko, Eric. M. Monberg, Hongchao Wu, Debra A. Simoff, Thierry F. Taunay, Roy. M. Ortiz , "Continuous multicore optical fiber grating arrays for distributed sensing applications", Journal of Lightwave Technology, v PP, Issue 99, pp. 1-5, doi:10.1109/JLT.2017.2661680, 2017.
Aleksandar Lukic, Sebastian Dochow, Hyeonsoo Bae, Gregor Matz, Ines Latka, Bernhard Messerschmidt, Michael Schmitt, and Jürgen Popp, "Endoscopic fiber probe for nonlinear spectroscopic imaging", Optica, v 4, No. 5, https://doi.org/10.1364/OPTICA.4.000496, 2017.
J. Carpenter, B. J. Eggleton, and J. Schröder, "110 x 110 optical mode transfer matrix inversion", Opt. Express, vol. 22, pp. 96-101, 2014.
Joel Carpenter, "Everything you always wanted to know about Multimode Fiber", IEEE Photonics Society Newsletter, pp. 4-10, Aug. 2017.
Youngwoon Choi, Changhyeong Yoon Moonseok Kim Taeseok Daniel Yang Christopher Fang-Yen, Ramachandra R. Dasari, Kyoung Jin Lee, and Wonshik Choi, "Scanner-Free and Wide-Field Endoscopic Imaging by Using a Single Multimode Optical Fiber" Physical Review Letters, vol. 109, 203901, Nov. 2012.
Silvio Bianchi and Roberto Di Leonardo, "A multi-mode fiber probe for holographic micromanipulation and microscopy", Lab on a Chip, V. 121, 635, 2012.
T. S. Ralston, D. L. Marks, P. S. Carney, S. A. Boppart, "Interferometric synthetic aperture microscopy". Nature Physics, 3, (2), 129-134, 2007.
J. Carpenter, B. J. Eggleton, and J. Schröder, "Observation of Eisenbud-Wigner-Smith states as principal modes in multimode fibre," Nat Phot., vol. 9, No. 11, pp. 751-757, Nov. 2015.

(56) References Cited

OTHER PUBLICATIONS

J. Carpenter, B. J. Eggleton, and J. Schröder, "Comparison of principal modes and spatial eigenmodes in multimode optical fibre," Laser Photon. Rev., Dec. 2016.

J. Carpenter, B. J. Eggleton, and J. Schröder, "First demonstration of principal modes in a multimode fibre," in European Conference on Optical Communication, ECOC, 2014.

S. Fan and J. M. Kahn, "Principal modes in multimode waveguides," Opt. Lett, vol. 30, pp. 135-137, 2005.

J. Carpenter, B. J. Eggleton, and J. Schröder, "Complete spatiotemporal characterization and optical transfer matrix inversion of a 420 mode fiber," Opt. Lett., vol. 41, No. 23, pp. 5580-5583, 2016.

Bo Shuang, Wenxiao Wang, Hao She, Lawrence J. Tauzin, Charlotte Flateb, Jianbo Chen, Nicholas A. Moring, Logan D. C. Bishop, Kevin F. Kelly & Christy F. Landes, "Generalized recovery algorithm for 3D super-resolution microscopy using rotating point spread Functions", Scientific Reports, 6:30826, DOI: 10.1038/srep30826, 2016.

Ioannis N. Papadopoulos, Salma Farahi, Christophe Moser, and Demetri Psaltis, "Focusing and scanning light through a multimode optical fiber using digital phase conjugation", Optics Express, V. 20, No. 10, 2012.

A. M. Caravaca-Aguirre, E. Niv, and R. Piestun, "High-speed phase modulation for multimode fiber endoscope," Imaging Appl. Opt. (2014).

R. Y. Gu, R. N. Mahalati, and J. M. Kahn, "Noise-reduction algorithms for optimization-based imaging through multi-mode fiber," Opt. Express 22(12), 15118-15132 (2014).

D. Loterie, S. Farahi, I. Papadopoulos, A. Goy, D. Psaltis, and C. Moser, "Digital confocal microscopy through a multimode fiber," http://arxiv.org/abs/1502.04172 (2015).

E. E. Morales-Delgado, S. Farahi, I. N. Papadopoulos, D. Psaltis, and C. Moser, "Delivery of focused short pulses through a multimode fiber", Opt. Express 23(7), 9109-9120 (2015).

Y. Choi C. Yoon, M. Kim, W. Choi, and W. Choi, "Optical imaging with the use of a scattering lens", IEEE J. Sel. Top. Quantum Electron. 20(2), 61-73 (2014).

S. Bianchi, V. P. Rajamanickam, L. Ferrara, E. Di Fabrizio, R. Di Leonardo, and C. Liberale, "High numerical aperture imaging by using multimode fibers with micro-fabricated optics", in CLEO: Science and Innovations (OSA, 2014), paper SM2N.6.

M. Plöschner and T. Čižmár, "Compact multimode fiber beam-shaping system based on GPU accelerated digital holography", Opt. Lett. 40(2), 197-200 (2015).

A. M. Caravaca Aguirre and R. Piestun, "Robustness of multimode fiber focusing through wavefront shaping", in Latin America Optics and Photonics Conference (2014).

S. Farahi, D. Ziegler, I. N. Papadopoulos, D. Psaltis, and C. Moser, "Dynamic bending compensation while focusing through a multimode fiber", Opt. Express 21(19), 22504-22514 (2013).

R. A. Panicker and J. M. Kahn, "Algorithms for compensation of multimode fiber dispersion using adaptive optics", J. Lightwave Technol. 27(24), 5790-5799 (2009).

R. A. Horn, Matrix Analysis, 2nd ed. (Cambridge University, 2013). 24. M. Sasaki, T. Ando, S. Nogawa, and K. Hane, "Direct photolithography on optical fiber end", Jpn. J. Appl. Phys. 41(Part 1, No. 6B), 4350-4355 (2002).

Antonio M. Caravaca-Aguirre, Eyal Niv, Donald B. Conkey, and Rafael Piestun, "Real-time resilient focusing through a bending multimode fiber", Optics Express, vol. 21, No. 10, DOI:10.1364/OE.21.012881, (2013).

Paul H. Beckwith, Ian McMichael, and Pochi Yeh, "Image distortion in multimode fibers and restoration by polarization-preserving phase conjugation", Optics Letters, vol. 12, No. 8, 1987.

D. Z. Anderson, M. A. Bolshtyansky and B. Ya. Zel'dovich, "Stabilization of the speckle pattern of a multimode fiber undergoing bending", Optics Letters, vol. 21, No. 11, Jun. 1996.

"International Search Report and Written Opinion" for International Patent Application No. PCT/US19/13123, dated Apr. 8, 2019, 8 pages, ISA/US, Commissioner for Patents, Alexandria VA, US.

C. Boudoux, et al., Rapid wavelength-swept spectrally encoded confocal microscopy, Optics Express, Oct. 3, 2005, pp. 8214-8221, vol. 13, No. 20, OSA.

Dongyao Cui, et al., Multifiber angular compounding optical coherence tomography for speckle reduction, Optics Letter, Jan. 1, 2017, pp. 125-128, vol. 42, No. 1, Optical Society of America.

Daniel J. Fechtig, et al., Line-field parallel swept source MHz OCT for structural and functional retinal imaging, Biomedical Optics Express, Mar. 1, 2015, pp. 716-735, vol. 6, No. 3, OSA.

Simon Lemire-Renaud, et al., Double-clad fiber coupler for endoscopy, Optics Express, May 10, 2020, 9755-9764, vol. 18, No. 10, OSA.

Florence Rossant, et al., Highlighting directional reflectance properties of retinal substructures from D-OCT images, IEE Transactions on Biomedical Engineering, Nov. 2019, pp. 3105-3118, vol. 66, No. 11, EMB.

Seon Young Ryu, et al., Combined system of optical coherence tomography and fluorescence spectroscopy based on double-cladding fiber, Optics Letters, pp. 2347-2349, Oct. 15, 2008, vol. 33, No. 20.

Juan Sancho-Dura, et al., Handheld multi-modal imaging for point-of-care skin diagnosis based on akinetic integrated optics optical coherence tomography, Biophotonics Journal, 2018, pp. 1-6, 2018, Wiley-VCH Verlag, GmbH & Co. KGaA Weinheim.

Tuqiang Xie, et al., Fiber-optic-bundle-based optical coherence tomography, Optics Letters, Jul. 15, 2005, pp. 1803-1805, vol. 30, No. 14.

Gunay Yurtsever, et al., Photonic integrated Mach-Zehnder interferometer with an on-chip reference arm for optical coherence tomography, Biomedical Optics Express, Apr. 1, 2014, pp. 1050-1060, vol. 5, No. 4, OSA.

Chao Zhou, et al., Space-division multiplexing optical coherence tomography, Optics Express, Aug. 12, 2013, pp. 19219-19227, vol. 21, No. 16, OSA.

Simon Lemire-Renaud, et al.; Double-Clad Fiber Coupler for Endoscopy, May 10, 2010, pp. 9755-9764, vol. 18, No. 10, Optics Express.

Seon Young Ryu, et al.; Combined System of Optical Coherence Tomography and Fluorescence Spectroscopy Based on Double-Cladding Fiber, Oct. 15, 2008, pp. 2347-2349, vol. 33, No. 20, Optics Letters.

Manon Rostykus, and Christophe Moser, "Compact lensless off-axis transmission digital holographic microscope," Opt Ex. 25(14), 16652-16659 (2017).

Damien Loterie, Demetri Psaltis, and Christophe Moser, "Bend translation in multimode fiber imaging," Opt. Ex. 25(6), 6263-6273 (2017).

Edgar E. Morales-Delgado, Demetri Psaltis, and Christophe Moser, "Two-photon imaging through a multimode fiber," Opt. Ex. 23(25), 32158-32170 (2015).

Damien Loterie, Sebstianus A. Goorden, Demetrie Psaltis, and Christophe Moser, "Confocal microscopy through a multimode fiber using optical correlation," Opt. Lett. 40(24), 5754-5757 (2015).

Siddharth Sivankutty, Esben Ravn Andresen, Rosa Cossart, Geraud Bouwmans, Serge Monneret, and Herve Rigneault, Ultra-thin rigid endoscope: two-photon imaging through a graded-index.

Sean C. Warren, Youngchan Kim, James M. Stone, Claire Mitchell, Jonathan C. Knight, Mark A. A. Neil, Carl Paterson, Paul M. W. French, and Chris Dunsby, "Adaptive multiphoton endomicroscopy through a dynamically deformed multicore optical fiber using proximal detection," Opt. Ex. 24(19), 21474-21484 (2016).

Alexander Fertman and Dvir Yelin, "Image transmission through an optical fiber using real-time modal phase restoration," JOSAB 30(1), 149-157 (2013).

Mickael Mounaix, Hilton B. de Aguiar, and Sylvain Gigan, "Temporal recompression through a scattering medium via a broadband transmission matrix," ArXiv (2017).

S. M. Popoff, G. Lerosey, R. Carminati, M. Fink, A.C. Boccara, and S. Gigan, "Measuring the Transmission Matrix in Optics : An Approach to the Study and Control of Light Propagation in Disordered Media," Phys. Rev. Lett. 104(10), 100601-100605 (2010).

(56) References Cited

OTHER PUBLICATIONS

Jürgen W. Czarske, Daniel Haufe, Nektarios Koukourakis, and Lars Milner, "Transmission of independent signals through a multimode fiber using digital optical phase conjugation," Opt. Ex. 24(13), 15128-15136 (2016).

J. M. Stone, H. A. C. Wood, K. Harrinton, and T. A. Birks, "Low index contrast imaging fibers," Opt. Lett. 42(8), 1484-1487 (2017).

Harry A. C. Wood, Kerrianne Harrington, James M. Stone, Tim A. Birks, and Jonathan C. Knight, "Quantitative characterization of endoscopic imaging fibers," Opt. Ex. 25(3), 1985-1992 (2017).

Antonio M. Caravaca-Aguirre and Rafael Piestun, "Single multimode fiber endoscope," Opt Ex. 25(3), 1656-1665 (2017).

Ivan Gusachenko, Mingahou Chen, and Kishan Dholakia, "Raman imaging through a single multimode fibre," Opt. Ex. 25(12), 13782-13798 (2017).

Tomas Cizmar, and Kishan Dholakia, "Shaping the light transmission through a multimode optical fibre: complex transformation analysis and applications in biophotonics," Opt. Ex. 19(20), 18871-8884 (2011).

Moussa N'Gom, Theodore B. Norris, Eric Michielssen, Raj Rao Nadakuditi, "Mode Control in a Multimode Fiber Through Acquiring its Transmission Matrix from a Reference-less Optical System," ArXiv (2017).

Roberto Di Leonardo and Silvio Bianchi, "Hologram transmission through multi-mode optical fibers," Opt. Ex. 19(1), 247-254 (2011).

Carmelo Rosales-Guzman, Nkosiphile Bhebhe, Nyiku Mahonisi, and Andrew Forbes, "Multiplexing 200 modes on a single digital hologram," ArXiv (2017).

Peng Lu, Matthew Shipton, Anbo Wang, Shay Soker, and Yong Xu, "Adaptive control of waveguide modes in a two-mode fiber," Opt. Ex. 22(3), 2955-2964 (2014).

Shamir Rosen, Doron Gilboa, Ori Katz, Yaron Silberberg, "Focusing and Scanning through Flexible Multimode Fibers without Access to the Distal End", 8 pages.

Pablo Eugui, Antonia Lichtenegger, Marco Augustin, Danielle J. Harper, Martina Muck, Thomas Roetzer, Andreas Wartak, Thomas Konegger, Georg Widhalm, Christoph K. Hitzenberger, Adelheid Woehrer, and Bernhard Baumann, Beyond backscattering: Optical neuroimaging by BRAD, arXiv:1712.00361v1 [physics.optics] Dec. 1, 2017.

Carmelo Rosales-Guzmán and Andrew Forbes, "How to Shape Light with Spatial Light Modulators", SPIE Spotlight, doi: http://dx.doi.org/10.1117/3.2281295, 2017.

Lucas B. Soldano and Erik C. M. Pennings, "Optical Multi-Mode Interference Devices Based on Self-Imaging: Principles and Applications", Journal of Lightwave Technology, vol. 13, No. 4, Apr. 1995.

Victor Arrizón, Ulises Ruiz, Rosibel Carrada, and Luis A. González, "Pixelated phase computer holograms for the accurate encoding of scalar complex fields", J. Opt. Soc. Am. A/vol. 24, No. 11/Nov. 2007.

Jeff Demas, Lars Rishøj, and Siddharth Ramachandran, Free-space beam shaping for precise control and conversion of modes in optical fiber, vol. 23, No. 22 DOI:10.1364/OE.23.028531, 2015.

S. M. Popoff, G. Lerosey, R. Carminati, M. Fink, A.C. Boccara, S. Gigan, "Measuring the Transmission Matrix in Optics: An Approach to the Study and Control of Light Propagation in Disordered Media", arXiv:0910.5436v2 [physics.optics] Jan. 18, 2010.

James G. Fujimoto, Eric Swanson, Robert Huber, European Inventor Award 2017, Jun. 15, 2017, 3 pages. PRWeb.

* cited by examiner

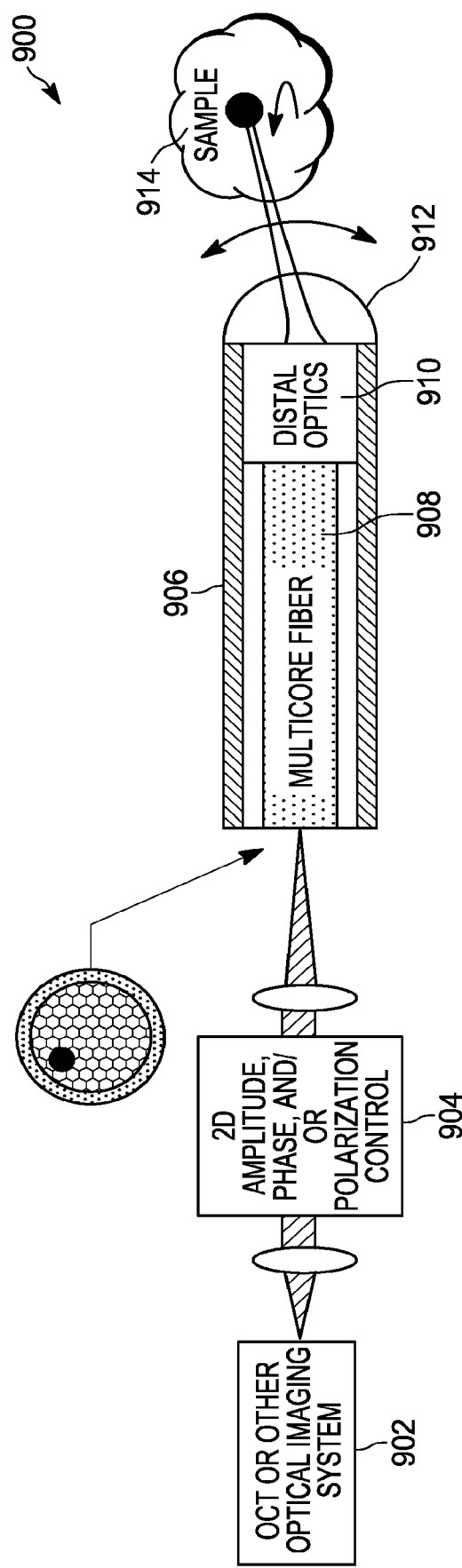
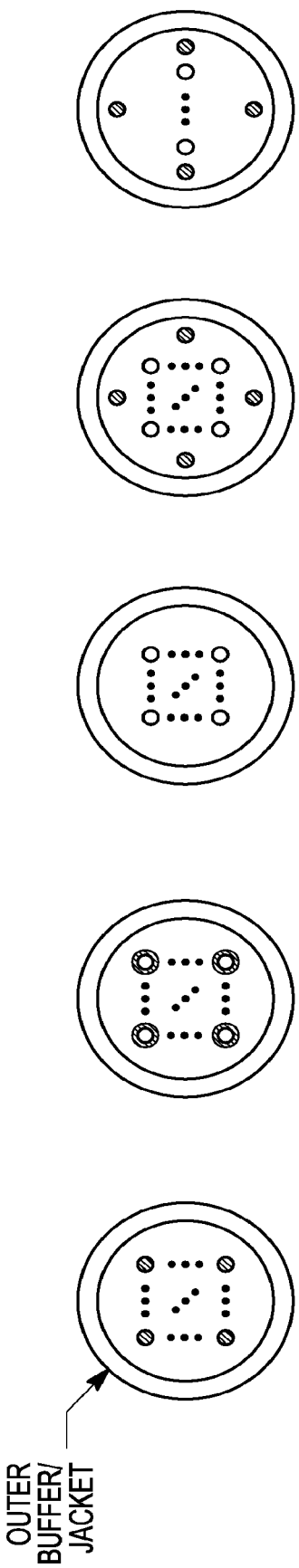
FIG. 9A
FIG. 9B
FIG. 9C
FIG. 9D
FIG. 9E
FIG. 9F

OPTICAL PROBE

CROSS REFERENCE TO RELATED APPLICATION

The present application is a continuation of U.S. patent application Ser. No. 15/868,521, filed on Jan. 11, 2018, entitled "Optical Probe Using Multimode Optical Waveguide and Proximal Processing". The entire contents of U.S. patent application Ser. No. 15/868,521 are herein incorporated by reference.

The section headings used herein are for organizational purposes only and should not to be construed as limiting the subject matter described in the present application in any way.

INTRODUCTION

The present teaching relates to medical and non-medical applications for delivering and/or collecting light, and/or performing optical imaging and/or performing optical therapy of a sample at the distal end of an optical waveguide. In some embodiments, optical properties of a sample are determined. Optical properties can include, for example, absorption, reflection, refractive index, birefringence, dispersion, fluorescence, and other properties and this can be a function of wavelength and be at a point, a small volume, and/or spatially or spectrally resolved along one dimension, or multiple dimensions.

There are many medical and non-medical needs for performing optical imaging of a sample (e.g. human organ or sample in hard to reach places). This includes within the human body to perform diagnostic or therapeutic procedures. To deliver light to and/or collect light from hard to reach tissue regions of interest, there are a variety of devices and approaches such as those shown in FIG. 1. This includes endoscopes 100, catheters 120, guidewires, laparoscopes, trocars 140, borescopes, needles, and various minimally invasive and robotic surgical devices. To perform one, two, or three dimensional imaging and/or functional imaging, there are a variety of possible modalities including optical coherence tomography (OCT) and other interferometry-based imaging, confocal microscopy, spectroscopic imaging, fluorescence imaging, Raman imaging, multi-photon imaging, and reflectance imaging, etc. Each imaging modality offers distinct attributes. For example, OCT can achieve high axial sub-Rayleigh range resolution due to the coherence gating of the OCT imaging process, which can be highly beneficial in a wide range of scenarios where high-resolution axial optical property information and long depth-of-field is desirable. For comparison, fluorescence imaging can more readily provide molecular information but, usually has less depth-of-field. In many applications, it is useful to deliver light for therapy, such as laser ablation and photodynamic therapy.

Single-mode optical fibers are inexpensive and flexible and commonly used to transmit light along an endoscope, but single-mode fiber by itself typically cannot perform spatial 2D or 3D imaging. To perform imaging using a single-mode fiber usually requires scanning of the light emitted and/or collected from the single-mode fiber. There are a variety of existing techniques that enable scanning the optical beam at the distal end of an endoscope containing a single-mode fiber including using rotating single-mode fibers driving by torque cables, or distal motors illuminated by single-mode optical fibers, and other mechanical or electro-optic approaches such as those shown in FIG. 2 or described in the reference, "Methods and Apparatus for Forward-Directed Optical Scanning Instruments," S. A. Boppart, G. J. Tearney, B. E. Bouma, M. E. Brezinski, J. G. Fujimoto, and E. A. Swanson, U.S. Pat. No. 6,485,413, issued Nov. 26, 2002. For many important medical and non-medical applications, these existing techniques suffer from a variety of significant limitations such as: the endoscopic probe being too thick and/or not flexible enough to access important regions within the human body; an inability to fit inside existing ports of clinical instruments; the endoscope or the system it attaches being too expensive; the endoscope being less reliable than desired; the scanning mechanism introducing optical image artifacts, such as non-uniform rotation distortion. A significant advance over these prior art limitations is needed to open up new clinical applications and to perform better in existing ones.

BRIEF DESCRIPTION OF THE DRAWINGS

The present teaching, in accordance with preferred and exemplary embodiments, together with further advantages thereof, is more particularly described in the following detailed description, taken in conjunction with the accompanying drawings. The person skilled in the art will understand that the drawings, described below, are for illustration purposes only. The drawings are not necessarily to scale, emphasis instead generally being placed upon illustrating principles of the teaching. The drawings are not intended to limit the scope of the Applicant's teaching in any way. Also note for simplicity some of the drawings show beam propagation (e.g. beam divergence) that is not to scale or proportion or exact location within the samples.

FIG. 9A illustrates an embodiment of a remote optical probe system of the present teaching.

FIG. 9B illustrates an embodiment of a cross section of a multicore fiber of the present teaching comprising multiple cores and a common cladding.

FIG. 9C illustrates an embodiment of a cross section of a multicore fiber of the present teaching comprising multiple cores each with separate claddings with optional absorptive or light stripping common cladding and/or buffer.

FIG. 9D illustrates an embodiment of a cross section of a multicore fiber of the present teaching comprising a hollow core multicore fiber with a coating to minimize core to core coupling.

FIG. 9E illustrates an embodiment of a cross section of a multicore fiber of the present teaching comprising a multi-core optical fiber in combination with one or several shape sensing fibers.

FIG. 9F illustrates an embodiment of a cross section of a multicore fiber of the present teaching comprising a multi-core fiber with a single row of cores, distributed along a one-dimensional line in any transverse plane that is perpendicular to the fiber axis, and also including shape sensing fibers.

DESCRIPTION OF VARIOUS EMBODIMENTS

Figure 1:
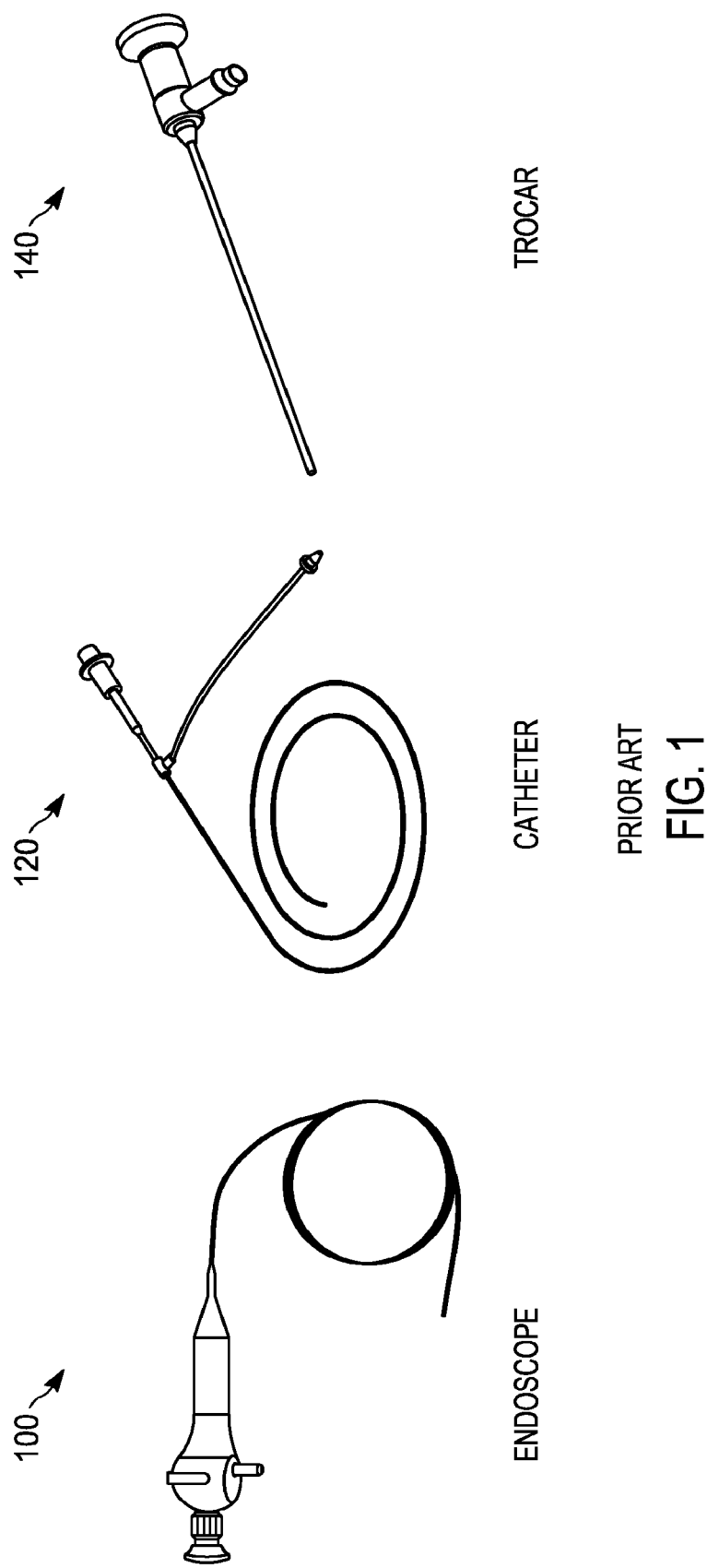
FIG. 1 shows examples of known medical optical imaging devices.

The present teaching will now be described in more detail with reference to exemplary embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill in the art having access to the teaching herein will recognize additional implementations, modifications, and embodiments, as well as other fields of use, which are within the scope of the present disclosure as described herein.

Reference in the specification to "one embodiment" or "an embodiment" means that a particular feature, structure, or characteristic described in connection with the embodiment is included in at least one embodiment of the teaching. The appearances of the phrase "in one embodiment" in various places in the specification are not necessarily all referring to the same embodiment.

It should be understood that the individual steps of the methods of the present teaching can be performed in any order and/or simultaneously as long as the teaching remains operable. Furthermore, it should be understood that the apparatus and methods of the present teaching can include any number or all of the described embodiments as long as the teaching remains operable. For example, it should be understood that the word "fiber" and the word "core" are used throughout the specification in a somewhat interchangeable manner. It will be understood by those of skill in the art that when multiple cores are described as embedded in a common cladding, there is an equivalent embodiment with multiple optical fibers, each with a core and a cladding embedded in a second outer common cladding. Such cores could be single-mode, few-mode, or multi-mode optical cores.

The present teaching relates to the many medical and non-medical applications for delivering and/or collecting light and/or performing optical imaging of a sample in hard to reach places. In this disclosure, we use the word "light" for any radiation, for example, in the wavelength range from ultraviolet to infrared, including the entire visible spectrum.

The use of multimode or multicore optical fiber according to the present teaching instead of single-mode optical fiber in an endoscope offers dramatic advantages for optical imaging because such optical fiber can support multiple spatial optical modes (instead of just one in single-mode fiber) allowing more complex optical fields to be measured and/or created at the distal end of the endoscope by manipulating or measuring the optical field at the proximal end of the endoscope or to recover a complex field at the proximal end of the endoscope from light emitted from a sample at the distal end of the endoscope. It should be understood that the terms "waveguide" and "fiber" are used interchangeably herein, as an optical fiber is a type of waveguide. It should also be understood that the term "endoscope" as used herein is intended to have a broad meaning to include medical devices such as catheters, guidewires, laparoscopes, trocars, borescopes, needles, and various minimally invasive and robotic surgical devices.

Figure 2:
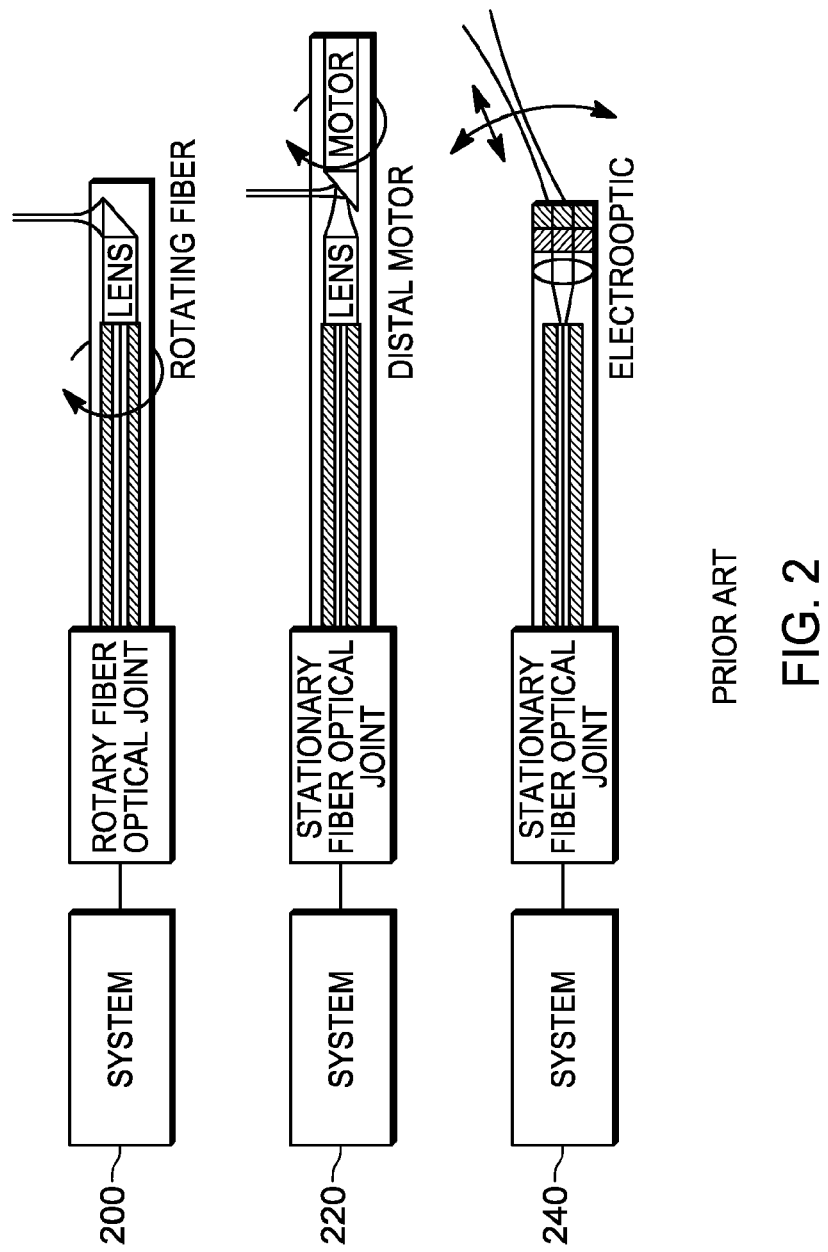
FIG. 2 shows examples of known distal optical scanning approaches.
Figure 3:
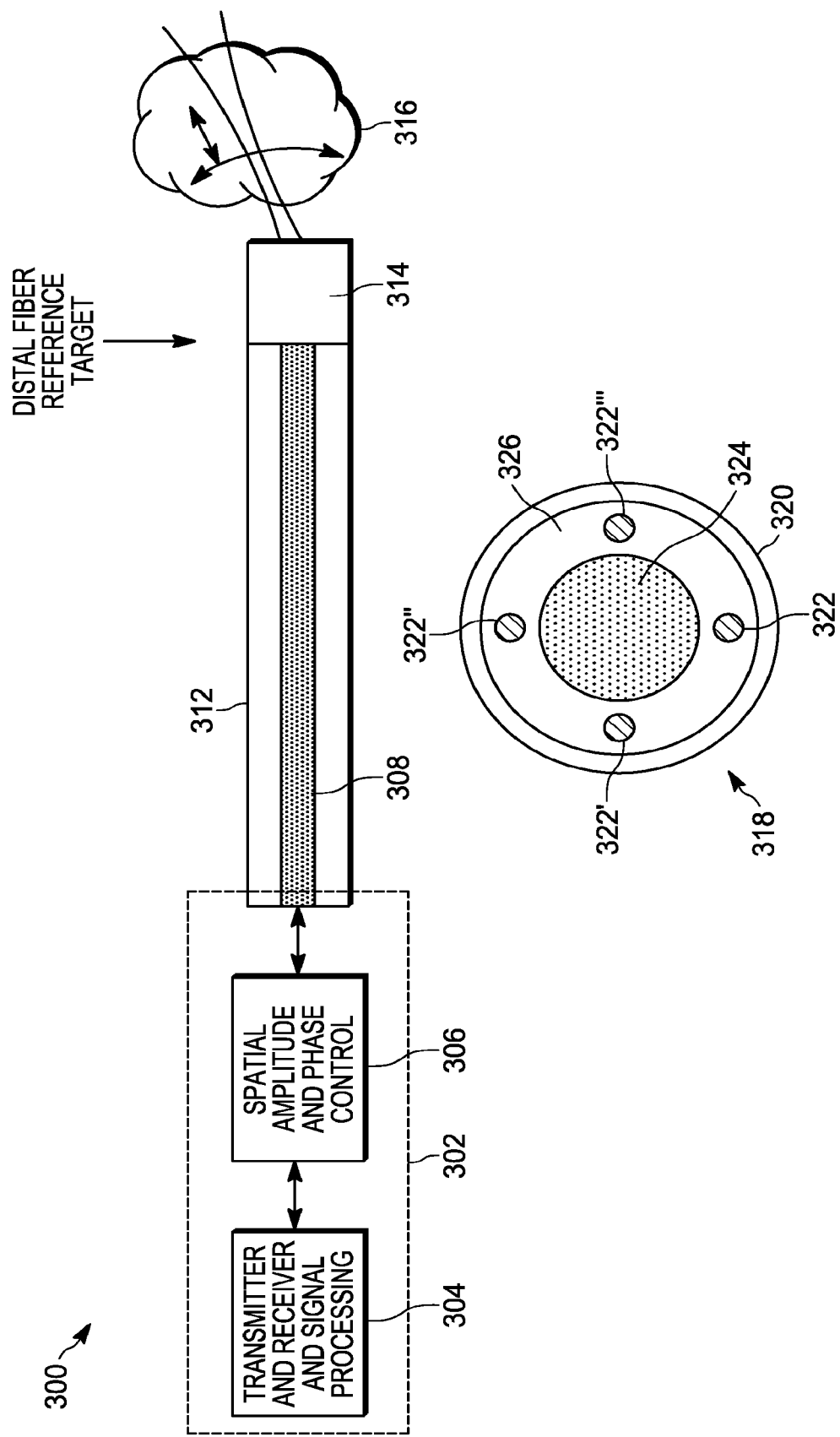
FIG. 3 illustrates a simplified diagram of one embodiment of the present teaching containing a processing system and a multicore fiber containing single mode and multimode components.

A simplified example of such a system is shown in FIG. 3 where distal scanning of the focal spot is possible in either the lateral or longitudinal directions or both. Such an approach allows numerous benefits including a much smaller, lower cost, and more flexible endoscope containing multimode or multicore fiber than, for example, those shown in FIG. 2. But one mitigating issue is that propagation of the optical field from one end to the other end of the endoscope is complex and continuously changing in response to environmental disturbances, such as a doctor manipulating the endoscope, heart beating, breathing, temperature fluctuations, or other motion from a living patient or environmental disturbances. The transformation of the optical field from one end to the other end of the endoscope is sometimes referred to as a transfer function. The transformation performed by the fiber upon the optical field is sometimes referred to as a transfer function of the fiber. To accomplish imaging using a multimode fiber requires understanding and/or actively compensating for the continuously changing multimode fiber transfer function. Systems can utilize that transfer function to perform imaging to assess the optical properties of a sample and/or deliver light to the sample for therapy. For some embodiments of the present teaching, the power level in the fiber is sufficiently low such that nonlinearities can be neglected, i.e., the transfer function is independent of the launched light, in particular in its distribution among the different modes of the fiber. In this case, the transfer function is expressed by a transfer matrix. In other embodiments, these assumptions are relaxed with a corresponding change in computation and hardware complexity.

The following disclosure generally relates to the use of a multimode or multicore optical fiber connected to a system with processing located at the proximal end of the optical fiber and a sample located near the distal end of the fiber, where that processing can determine or otherwise compensate for the optical transfer function of the multimode or multicore optical fiber and use that information to perform optical imaging of a sample's optical properties, or scanning of light on a sample, or determining optical properties of the sample located near the distal end of the optical fiber. In some aspects of the present teaching, the system uses proximally control distal sources to aid in determining some of the spatial and/or temporal effects of the multimode or multicore optical fiber on the optical beam propagation along the optical fiber.

We now begin to describe one aspect of the present teaching imaging through a multimode fiber. There are known methods of beam steering of an optical field using phase and/or amplitude control of light over a multimode optical fiber. Also uni-directional imaging and illumination through multimode waveguides is known. Multimode endoscopes are also well known in the art. However, in known methods and apparatus, the transfer function of a multimode fiber has required access to both ends of the multimode waveguide or pre-calibration, with assumptions on the amount of external perturbations that can be tolerated, as well as further assumptions on the wavelength of light occupying a narrow optical bandwidth. These assumptions are not suitable for many endoscope applications, particularly those in a medical setting or those using broad-bandwidth light sources such as OCT. What is needed is a complete and robust solution for compensating for the continuously changing multimode transfer function using mainly proximal end processing of an endoscopic probe, or other remote optical probe device, in a perturbed environment as well as descriptions of imaging or light delivery and/or collection systems that can utilize that compensation.

There are a variety of existing methods and apparatus to access these hard to reach places such as endoscopes, catheters, guidewires, laparoscopes, trocars, borescopes, needles, and various minimally invasive and robotic surgical devices. FIG. 1 illustrates an endoscope 100, catheter 120, and trocar 140 that are prior art devices known to be used to deliver and collect light from hard to reach places.

FIG. 2 shows examples of prior art distal optical scanning approaches. A first prior art scanning approach 200 uses a rotary fiber optical joint and a rotating fiber. A second prior art scanning approach 220 uses a stationary fiber optical joint and a distal motor. A third prior art scanning approach 240 uses a stationary fiber optical joint and an electro-optic system for scanning.

For many of the applications that utilize the variety of existing methods and devices to access hard to reach places, the existing methods suffer from the device (e.g. endoscope) being too large, not flexible enough, too expensive, suffering from optical artifacts, and other limitations. This teaching describes techniques that overcome these and other limitations of known apparatus. For example, one embodiment of the present teaching includes the use of a multicore optical fiber with proximal processing that can determine the optical imaging transfer function of the optical fiber and use that information to perform optical imaging of the sample located at the distal end of the optical fiber.

The present teaching describes methods to achieve physical or synthetic scanning of light onto a sample and/or imaging of light emitting from sample (e.g. tissue) at the distal end of a primarily passive multimode and/or multicore fiber endoscope using mainly proximal end processing. There are extensions to the embodiments presented herein that will be recognizable to one skilled in the art, such as including features like optical gain and nonlinearities as well as combinations of the invention disclosed here and active electromechanical or electro-optical and passive imaging.

FIG. 3 illustrates a simplified diagram of one embodiment of the present teaching containing a processing system and a multicore fiber containing single mode and multimode components. FIG. 3 shows a diagram of one aspect of the present teaching. In particular, FIG. 3 illustrates an optical probe apparatus 300 that provides light delivery and collection and/or imaging of a sample 316 that could be located in a hard to reach place. A processing system 302 includes a subsystem 304 that comprises a transmitter and receiver and signal processing and a subsystem 306 that provides spatial amplitude and/or phase and/or wavelength and/or polarization control is connected to a multicore fiber 308 using a connector located near the proximal end (not shown). Subsystem 306 generates a spatial amplitude and/or phase and/or polarization profile on an optical beam generated by the transmitter in subsystem 304 in response to an electrical input signal. The spatial amplitude and/or phase profile may be generated in one or two dimensions across the optical beam. The spatial amplitude and phase profile may be modulated as a function of time and/or in response to control signals that may be generated by a processor that processes the signals received by the receiver of subsystem 304. The endoscope 312 includes a multicore fiber 308 containing single mode and multimode components (other types of fiber are also possible as described later). An optional distal optical module 314 is shown that assists in smooth navigation and/or imaging, scanning or collecting light from the distal sample 316 as well as, in some cases, in aiding in processing to determine the fiber transfer function. Light collected from the sample 316 and propagated along the multicore fiber 308 toward the receiver of subsystem 304. This light, sometimes referred to as measurement light or light from the sample, is used to determine an image or collect some other parameter or information of the distal sample 316. An example endoscope and fiber cross section 318 is also shown. This figure illustrates a simplified sheath and buffer and other common endoscope structure 320 that surround the multicore fiber cross section. The multicore fiber cross section includes single mode (or few mode) fibers 322, 322', 322'', 322'''. The region 324 may be a multimode core or comprise multiple fiber cores, which may be multi-mode or single-mode at operating wavelength. Note in FIG.

3 and other figures and associated text, the fibers indicated (e.g. fibers 322, 322', 322", 322'") may be a simple core surrounded by a common cladding (e.g. cladding 326) or they may be more complex structures such that contain both a core and cladding sounded by a second cladding (e.g. cladding 326). The fiber core region 324 is surrounded by a cladding 326. As described later, there are a wide variety of other fiber cross sections that can be used and are in keeping with this invention. Also as described later there are a variety of uses of fibers 322, 322', 322", and 322'" including acting as proximally controlled distal sources, shape sensing fibers, imaging fibers, actuation, or other functions. There can be more or fewer fiber cores than shown in FIG. 3. It is also possible to use several single core fibers that are bonded together.

The apparatus 300 shown in FIG. 3 can achieve low cost, small size, good flexibility, enhanced optical capabilities, and is highly suitable for one, two, or three-dimensional (3D) imaging and/or functional imaging, and has numerous other benefits for a variety of medical and non-medical applications. One aspect of the present teaching is actively measuring and/or compensating for the multimode fiber transfer function of the multicore fiber 308. This multimode fiber transfer function can be determined continuously or intermittently, depending on the application needs. Compensation of the fiber transfer function can be accomplished using several different methods. For example, one method uses physical compensation with a hologram or a spatial light modulator. Another method uses digital compensation using an algorithm, such as in a hill-climbing, simulated annealing or genetic algorithm optimization scheme. Yet another method uses computational compensation that applies a transformation matrix or other mathematical manipulation to the launched or detected optical field. In the presence of material and waveguide dispersion, the multimode transfer function may need to be known for all wavelengths that are being used by the imaging algorithm, which is important for applications such as swept-source optical coherence tomography (SS-OCT) or near-infrared (NIR) embodiments. However, if the modal properties are sufficiently constant or depend approximately linearly or in a known fashion on the wavelength in the spectral range used for the imaging, it may be sufficient to calibrate only at a single wavelength, e.g., in the center of the employed range of imaging wavelengths, or alternatively at a few distinct wavelengths (e.g., at the borders of the range of wavelengths) with subsequent interpolation. The round-trip calibration may also be performed for two polarizations at each wavelength. More generally, it is possible to use polarization diversity detection to obtain the full polarization information.

Once the optical multimode transfer function is known, there are several methods for delivering light to the distal sample and/or obtaining information about the sample's optical properties including: 1) adjusting the spatial and other optical properties of proximal light from the transmitter at the input to the multimode fiber to perform focusing, scanning or other manipulation of the light into the distal sample; 2) performing optical imaging by collecting the distal light emitted from the sample and correcting for the corruption of that collected light as it traverses the multimode optical fiber to the proximal end; 3) performing physical or synthetic confocal imaging or scanning where focused light is both delivered to and collected from the sample; 4) performing dark-field imaging or similar approaches where a focused beam is delivered to the sample and higher-order modes are collected and analyzed to determine information about the sample's optical properties; 5) performing focused spot scanning of light on the sample while having wide-area light collection (light of the same wavelength or different wavelength) using the cladding or a second additional outer cladding not shown; and 6) performing wide-area illumination of the sample and focused beam scanning of collected light. There are a variety of different embodiments of the system according to the present teaching, including interferometric based imaging (e.g. OCT), confocal microscopy, fluorescence imaging, multi-photon imaging, spectroscopic imaging, reflectance imaging, and Raman imaging, etc. One skilled in the art will appreciate that there are numerous other applications of the apparatus and method of the present teaching.

To determine a multimode fiber transfer function of a particular multicore and/or multimode optical fiber system requires control and/or measurement of the optical properties (e.g., spatial distribution of amplitude, phase, polarization, and/or wavelength) of light launched into and collected from the proximal end of a multimode/multicore fiber. In one embodiment, the fiber consists of a multicore fiber with at least one multimode fiber and one or more single mode fibers. Referring to FIG. 3, for example, four single mode fibers 322, 322', 322", 322'" are shown, as well as the multimode core region 324. The purpose of the single mode fibers in a multicore fiber of the present teaching is to deliver one or more proximally controlled distal sources to the distal end. These fibers can also serve other functions independently or simultaneously such as serving as proximally controlled distal sources and function as shape sensing fibers. This delivery of proximally controlled light to the distal end aids in the ability to determine the multimode fiber transfer function without requiring physical access to the distal end. The prior art methods do not give sufficient information about the actual distribution of the power among the different modes or the actual fiber transfer function.

One feature of some embodiments of the present teaching is that knowledge of the fiber transfer function is used by the processor in the optical probe system to deliver light and/or determine optical properties or other features of a sample. The determination of the fiber transfer function and utilization of that knowledge to deliver light or determine optical properties of the sample is described below.

One embodiment of the apparatus of the present teaching includes a multicore optical fiber containing multiple single-mode optical cores with minimal coupling between cores. A part of the light traveling in each core is being reflected at the distal fiber end and/or by a special reflector close to the distal fiber end. A part of the remaining transmitted light propagates to a sample where it is partially reflected. The light reflected from the distal fiber end or reflector is one form of light used for calibration of the system and may be referred to as calibration light. There are individual amplitude and phase adjusters at the proximal end of each fiber core that function as beam forming elements. A system controller actively measures the optical distance to the distal fiber reflections and adjusts the proximal amplitude and phase beam forming elements to implement the desired scan pattern of the distal light, e.g., in a manner analogous to phase array scanning. Synthetic processing approaches are also possible.

Some embodiments of the present teaching include combining an imaging fiber with simultaneous shape sensing and/or the ability to articulate the optical fiber from the proximal end to assist in determining the path and/or navigating torturous channels in the human body.

There are numerous aspects of the apparatus and methods for fiber optic imaging and light delivery and collection of the present teaching. Methods to determine and/or compensate for the continuously changing fiber transfer function are described. Systems and methods are also described that, once the transfer function is known, can deliver light to a sample, collect light from a sample, and/or perform imaging of the sample's optical properties. One aspect of the present teaching is that the transfer function of a multimode fiber is determined in a calibration step and then the input light spatial distribution (e.g. amplitude and/or phase) is adjusted to control the spatial distribution of the light at the distal end, e.g., to achieve physical focusing and scanning of the sample probe light on the sample.

Another aspect of the present teaching is that part of a calibration step and an imaging step is combined so that there is synthetic focusing and/or scanning of the distal light on the sample.

Another aspect of the present teaching is that a multicore fiber is used within an endoscope and each core has distal reflections and a proximal system interferometrically collects light from both the distal reflections and the sample and adjusts proximal amplitude and/or phase beam forming elements to perform distal scanning or imaging. The light collected from the distal reflections may be referred to as calibration light, and the light modified by the proximal amplitude and phase beam forming elements may be referred to as sample probe light.

Another aspect of the present teaching is that imaging, in combination with shape sensing and/or articulation, is realized. With respect to imaging, there are a variety of different embodiments according to the present teaching, including interferometry-based imaging (e.g. OCT), confocal microscopy, fluorescence imaging, multi-photon imaging, spectroscopic imaging, and reflectance imaging, etc.

Figure 4:
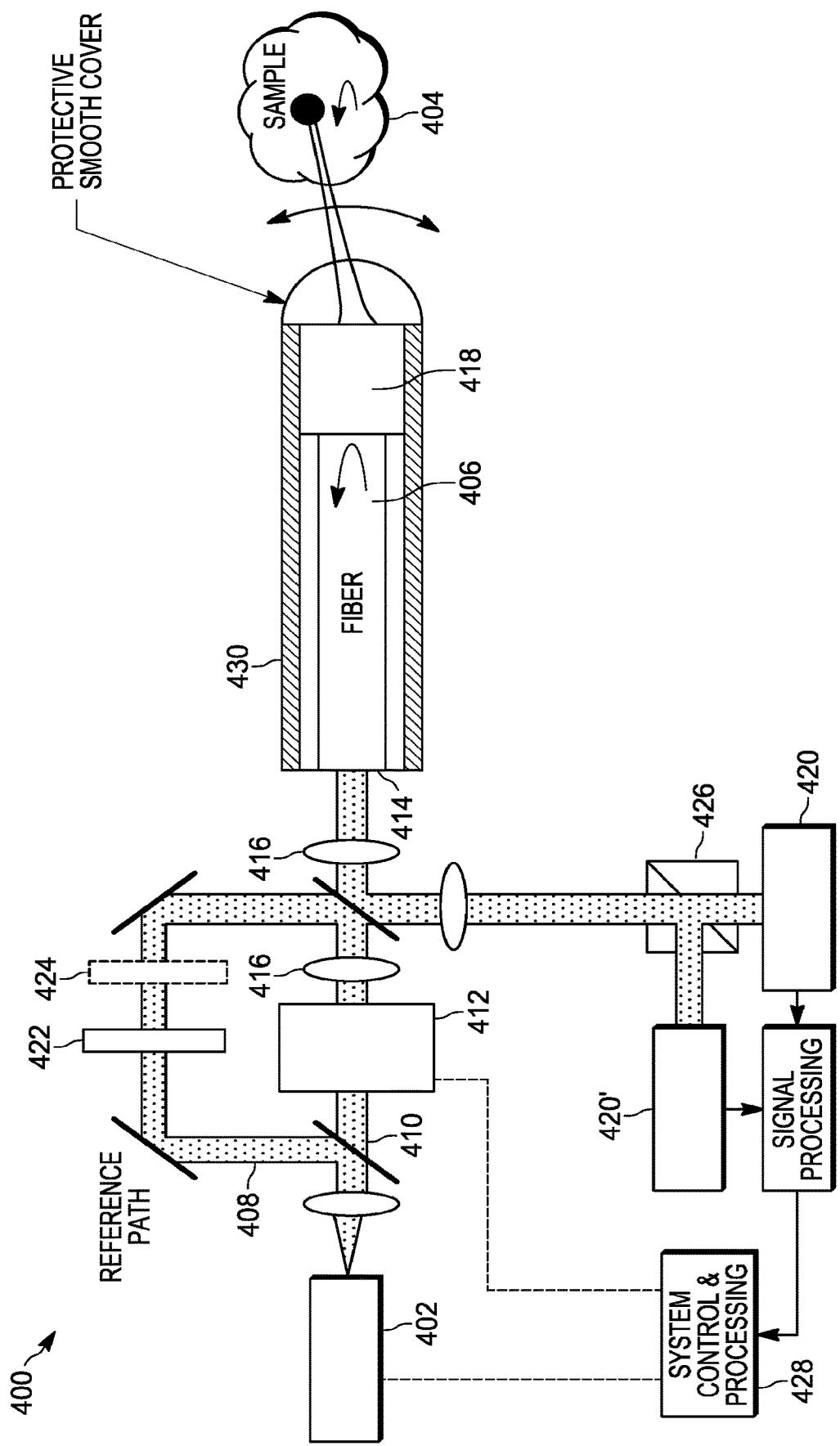
FIG. 4 shows an embodiment of a remote optical probe system of the present teaching in which polarization diversity detection is utilized.

FIG. 4 illustrates an embodiment of an endoscopic system 400 of the present teaching. A laser or other type of optical source 402 produces light at a proximal end of the endoscopic system 400. In some embodiments, the laser source 402 can be a swept-source OCT (SS-OCT) laser and the system 400 can be used for performing synthetic or physical scanning of the sample's optical properties. This is similar to a standard SS-OCT scan but with the important addition of having the endoscope contain a multimode optical fiber instead of a traditional single mode optical fiber in combination with scanning techniques. For example, a prior art traditional single mode optical fiber in combination with scanning techniques are shown in FIG. 2. In some embodiments, the optical source 402 laser wavelength is fixed and once the multimode fiber transfer function is known, the system implements physical scanning of the laser light onto the sample 404. This is useful in microscopy applications such as confocal, fluorescence, or multiphoton microscopy. The collection of the light can be in a confocal arrangement or wide-field detection. Alternatively, the multiple modes of the multimode waveguide 406 can be used to collect more light if single spatial mode detection imaging is not required. FIG. 4 does not illustrate the concept of proximally control distal sources (as described in more detail below and shown in various figures such as FIGS. 6, 7, and 13), but it should be understood that such proximally controlled distal sources and other functions such as shape sensing fibers can be used in many embodiments.

Also, an additional cladding waveguide around the multimode waveguide 406 can be used to collect more light. The multimode waveguide 406 may be a multimode and/or multicore fiber. The multiple cores in the multicore fiber may be coupled, uncoupled, or a combination of both coupled and uncoupled. For fluorescence imaging or calibration applications, the reflected light is often emitted at a different wavelength and a different detector in the receiver can be inserted with a wavelength selective beam splitter, for example, to collect and detect the fluorescence light. In another aspect of the present teaching, both the illumination and collection wavelength are the same wavelength, and confocal detection is performed. There are obvious extensions to other modalities that one skilled in the art can implement once the fiber transfer function is obtained.

As shown in FIG. 4, light output from the laser or other type of optical source 402 is collected and split into a reference path 408 and a path 410 to an amplitude, phase, and/or polarization control device 412. The one or two-dimensional amplitude, phase, and/or polarization control device 412 is sometimes referred to as a spatial light modulator (SLM). However, a generic amplitude, phase, and/or polarization control device is intended in this teaching. The control device 412 generates a spatial profile on an optical beam generated by the light source 402 in response to an electrical input signal from processing element 428. The spatial profile may be generated in one or two dimensions across the optical beam. The spatial profile may be modulated as a function of time and/or in response to control signals that may be generated by a processor that processes the signals received by a detector 420 and/or 420'. The spatial profile of the optical beam is sometimes referred to as having a complex optical field. Each point of the optical field wavefront can be described by several attributes including optical properties such as magnitude (amplitude), phase, wavelength, and polarization.

The feature of control device 412 is the ability to controllably excite many or all the modes of the multimode waveguide 406 either individually or in combinations. In one specific embodiment, the control device 412 is a spatial light modulator consisting of many sub-elements. In other embodiments, the control device 412 consists of an angular scanning device or a combination of the two. Other types of devices are also possible. The fiber input facet 414 can be in a focal plane, pupil plane, or image plane of the control device 412 or in another location. The control device 412 can also include optional shutters and polarization control. Light from the control device 412 is transferred onto the input facet 414 of the optical fiber using lenses 416 or other known optical approaches. The waveguide 406 can be a multicore fiber including a combination of multimode and single-mode cores which may be optically coupled or uncoupled as described herein. There may also be more than one fiber which are bonded over some or all of their length.

The distal end of the multimode waveguide 406 may contain distal optics 418, that may be active or passive, and assist in transferring light to or from the sample 404 of interest and optionally include shutters and other devices. These shutters and other devices are described later. The distal end may also contain distal sources which assist in learning the transfer-function of the multimode or multicore fiber, which is described further below. The distal end may also include a distal fiber reference target which also aids in learning the transfer-function of the multimode or multicore fiber that constitutes the multimode waveguide 406. Light from the sample 404 is collected by the multimode waveguide 406 and directed to one or more detector arrays 420, 420'. The detector arrays may include a detector array 420 for the x-direction and a detector array 420' for the y-direction. Light from the optical source 402 is also transmitted along a reference path 408 through optional wave plates 422 and modulators 424 to the detector arrays 420 and 420'. The waveplates 422 can be used to adjust the polarization, and the modulator 424 can be used to impart various forms of modulation (intensity, phase, polarization, frequency/wavelength (e.g., acousto-optic modulator (AOM) etc.)) to aid in extracting and/or calibrating the interference signal on the detectors 420, 420'. These interference signal features include phase, frequency, polarization, amplitude, and wavelength etc. The subsequent figures do not show the optional modulator 424. However, it should be understood that approaches utilizing a modulator 424 (in either the reference or sample path) are often beneficial to separate a signal of interest from background interference and can be incorporated into various embodiments of the present teaching.

In the embodiment shown in FIG. 4, received light from both the reference path 408 and the multimode waveguide 406 are directed onto a polarization beam splitter 426 that sends x-polarized light to the detector X array 420 and y-polarized light to detector Y array 420'. In other embodiments, the system does not differentiate between the two polarizations, and the receiver processing is then simplified at the expense of polarization information. Lenses or other suitable approaches are used to transfer light from the input facet 414 of the multimode waveguide 406 onto the detector arrays in combination with light from the reference path 408. A simplified diagram of the endoscope 430 is shown, but it is understood that this may include other structures typically found in endoscopes, such as protective jackets, sheaths, torque cables, accessory ports, multi-clad fibers, housings, articulation, and motors, radio-opaque markers, etc.

In some applications, it is important to balance the path lengths of different optical paths. For example, in some applications it is important to increase the length of the reference path to match the path from the sample and back to get good interferometric signals.

There are various forms of detector arrays 420, 420' that can be utilized, such as those based on photo-diode arrays, CCDs, and other array detectors. As is known in the art, there are various ways to extract the interference signal, such as off-axis digital holography, separation based on intermediate frequency (i.f.) frequency, phase, frequency, amplitude, etc. There are also a wide variety of spatial light modulator approaches including transmissive and reflective devices using integrated photonics devices, liquid crystal devices, Liquid Crystal on Silicon (LCOS), Micro-Electro-Mechanical System (MEMS), holographic devices, deformable mirror devices used in combinations with filtered gratings, and many more.

Distal scanning can be performed either physically or synthetically. The system learns the transfer function of the multimode waveguide 406 in a calibration step by inputting light and measuring light propagating in the multimode waveguide 406, and this light may have been reflected from a distal fiber reference target. This can be done in a separate calibration step or done in parallel with an optical gate implementing a gating technique to separate the different origins of distal light. For example, coherence gating, range gating, wavelength gating, polarization gating, time gating, i.f. frequency or numerous other types of gating can be used. If gating is used, some or all of the duty cycle lost from the calibration step can be recovered, and calibration reference light and sample light can be simultaneously collected. The scan of the distal light can be the actual desired scan pattern (e.g. a focused beam) or it can be a synthetic one-dimensional (1D), two-dimensional (2D), or three-dimensional (3D) scan of the beam within the sample 404—where the beam is synthesized computationally from a mathematical function processing a series of other scan patterns. The reference light and light collected from the sample 404 are processed to acquire information about the sample's optical and/or physical properties. The system 400 can also be used to deliver light to the sample 404 for therapeutic applications alone, or in combination with the process of acquiring information about the sample's optical and/or physical properties.

The transfer function of the multimode waveguide 406 is continuously changing in response to environmental disturbances, and this dictates how fast the entire process of sweeping a full or partial set of multimode fiber modes must be completed. The endoscope 430 may have distal optics 418, such as a lens, to optimize the transfer of light to and from the sample 404. For example, focusing and compensation for any aberrations of the endoscope housing that the light passes through may be accomplished by the distal optics 418. In some embodiments as described below, there is a use of a distal fiber reference target reflection that reflects light from the distal end of the multimode waveguide 406 and is used in determining the transfer function of multimode waveguide 406. The distal fiber reference target can be located at the distal facet of multimode waveguide 406, within or on the distal surface of distal optics 418, or other locations. The distal optics 418 may also have fold mirrors to substantially redirect the light away from the primary access of the fiber that forms the multimode waveguide 406. The entire endoscope 430 may also contain some form of mechanical angular or lateral scanning using motors, pullback motors, torque cables, or other known approaches, such as those described in connection with FIG. 2.

In some embodiments, the distal lensing and aberration correction are implemented in the field emitted from the multimode waveguide 406 by controlling the optical field launched into the proximal end of the multimode fiber. This reduces the complexity of the distal optics 418. Extended depth of field formations, for example Bessel fields, can also be implemented. The generation of such fields at the distal end distal optics 418 can allow for a very simple design, very low cost of the disposable endoscope, very small size, and flexibility. In some embodiments, the distal optics 418 may have a shutter, or other means, to separate when light is collected from the sample and when light is collected from a distal fiber reflectance target. The collection of light from a distal fiber reflectance target is described below.

The fiber transfer function that describes the coupling and amplitude, phase, and polarization and other relationship among the optical modes during propagation must be sufficiently accurately determined to control the light at the distal end of the multimode waveguide 406 (e.g. scanning a focused light beam from the laser into the sample 404) or recovery of a useful image. Additionally, a scheme to accomplish spatial scanning of the sample 404 to illuminate and/or image the sample and/or create an image in 1D, 2D or 3D is required. The latter can be a physical or synthetic scan. These two issues will be addressed separately below.

While it is possible to obtain the transfer function or transfer matrix of an imaging waveguide by launching light at the proximal end and performing measurements at the distal end, many applications require that such a calibration be performed without access to the distal end. One feature of the present teaching is a method to calibrate a multimode imaging waveguide using only proximal control and measurement of the light. The calibration procedure has two parts.

In the first part of the calibration procedure, we perform a round trip calibration of a multimode probe that includes an imaging waveguide. In the round trip calibration, we launch one or more electric field (E-field) patterns at the proximal side of a multimode probe, e.g., by coupling light with a suitable transverse field distribution into the waveguide. These E-fields excite a linear combination of modes of the waveguide that propagate to the distal end of the multimode probe. In general, this includes not only guided modes, but also leaky modes and radiation modes. At the distal end, a portion of this light is reflected back to the proximal side. At the proximal side, the E-field pattern of this reflected calibration light is measured. This E-field is the round trip E-field. With a sufficient number of launched E-field patterns, it is possible to obtain the transfer matrix relating the launched and round trip E-fields. As described below, the round trip transfer matrix may not be sufficient to obtain the transfer matrix relating the proximal and distal E-fields.

We therefore include a second part in the calibration. The second part of the calibration relies on including in our imaging waveguide some additional optics that allow for the creation of a distal source whose E-field is known. We describe the properties of this source in detail below. The critical property of this distal source is that it either does not change, or changes in a known way, or deviates only by a negligible amount from a known way, when the imaging waveguide is bent, twisted, or otherwise perturbed. The second step in our calibration procedure then records the proximal E-field when the distal source is illuminated. Because the distal source is known, this measurement will eliminate the ambiguities that arise in extracting the single pass transfer matrix from the round trip transfer matrix.

Figure 5:
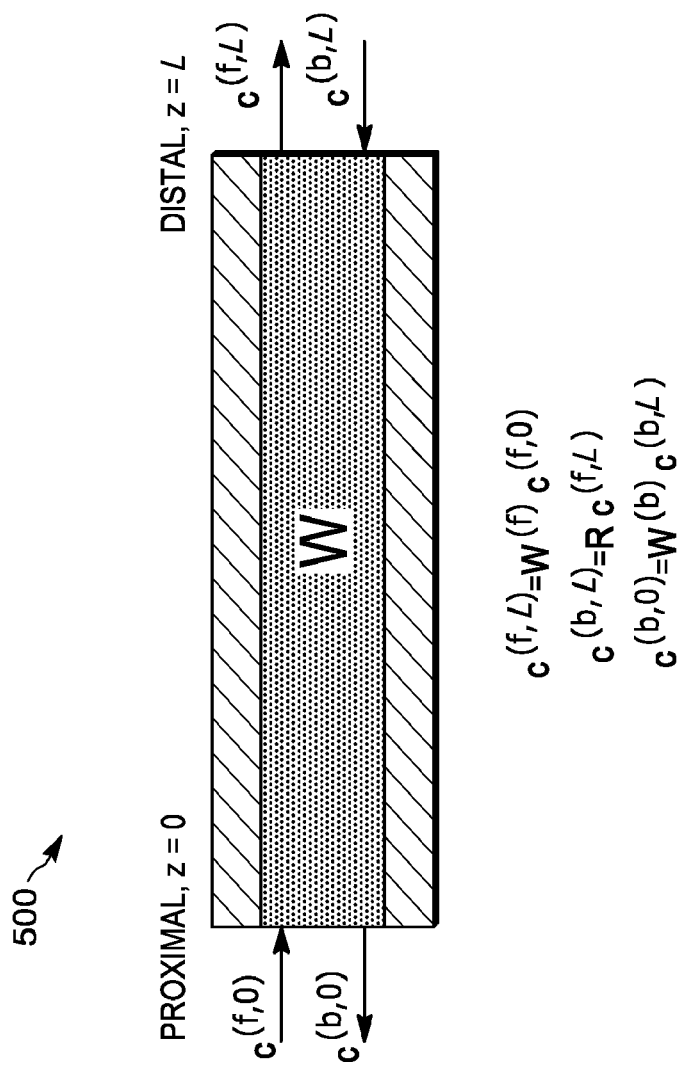
FIG. 5 shows a model of an embodiment of a multimode optical waveguide of the present teaching.

Below is a detailed description of part of the calibration procedure. FIG. 5 illustrates a model 500 of one embodiment of a multimode optical waveguide of the present teaching used in the calibration procedure. In the following, R is the set of real numbers, C is the set of complex numbers, and, e.g., $c \in C^N$ means that c is an N-dimensional vector with complex-valued entries. Furthermore, $\vec{E}$ refers to the three-dimensional physical E-field vector of the light. The transverse coordinates (x, y) span the transverse plane, which is perpendicular to a waveguide axis, along which the longitudinal coordinate z varies. In particular, z=0 is the proximal end of a remote probe, and z=L is the distal end of a remote probe. We assume that the number, N, of guided eigenmodes $\vec{E}(x, y, \lambda)$ of the multimode waveguide is sufficiently large such that the forward propagating light $\vec{E}_f(x, y, 0, \lambda)$ that has entered the multimode waveguide at the proximal end, z=0, can be written as a linear combination:

$$\vec{E}_f(x,y,0,\lambda) = \Sigma_{n=1}^N c_n^{(f,0)} \vec{E}_n(x,y,\lambda), \quad (1)$$

with the complex-valued coefficients $c_n^{(f,0)}$. This linear combination may include any type of guided modes, including different polarization modes and higher order modes. In absence of nonlinearities, the forward propagating light $\vec{E}_f(x, y, L, \lambda)$ that is about to exit the multimode waveguide at the distal end, z=L, can be similarly written as a linear combination:

$$\vec{E}_f(x,y,L,\lambda) = \Sigma_{n=1}^N c_n^{(f,L)} \vec{E}_n(x,y,\lambda), \quad (2)$$

with the complex-valued coefficients $c_n^{(f,L)}$. In absence of nonlinearities along the waveguide, and assuming that there is no coupling between forward and backward propagating fields along the waveguide (e.g., no Bragg grating along the waveguide or sufficiently low level of Rayleigh backscatter), there is a linear relation between the forward propagation coefficients at both ends of the waveguide, $$c^{(f,L)} = W^{(f)} c^{(f,0)}, \quad (3)$$

with the vectors $c^{(f,0)}$, $c^{(f,L)} \in C^N$ having entries $c_n^{(f,0)}$ and $c_n^{(f,L)}$, respectively, and the transfer matrix $W^{(f)} \in C^{N \times N}$ having entries $W_{m,n}^{(f)}$, with m, n=1, . . . , N. In presence of nonlinearities, the transfer function is usually more complicated than the matrix-vector multiplication from Eq. (3). In particular, the transfer matrix $W^{(f)}$ may then depend on the input $c^{(f,0)}$, and the output field $\vec{E}_f(x, y, L, \lambda)$ may no longer be a finite sum of only the guided modes.

In analogy to Eqs. (1)-(3), the E-fields and coefficients for the backward propagating fields satisfy the equations:

$$\vec{E}_b(x,y,0,\lambda) = \Sigma_{n=1}^N c_n^{(b,0)} \vec{E}_n(x,y,\lambda), \quad (4)$$

$$\vec{E}_b(x,y,L,\lambda) = \Sigma_{n=1}^N c_n^{(b,L)} \vec{E}_n(x,y,\lambda), \quad (5)$$

$$c^{(b,0)} = W^{(b)} c^{(b,L)}, \quad (6)$$

with the vectors $c^{(b,0)}$, $c^{(b,L)} \in C^N$ having entries $c_n^{(b,0)}$ and $c_n^{(b,L)}$, respectively, and the matrix $W^{(b)} \in C^{N \times N}$ having entries $W_{m,n}^{(b)}$, with m, n=1, . . . , N.

In absence of nonlinearities outside the waveguide, there is also a linear relation between the coefficients $c^{(f,L)}$ and $c^{(b,L)}$ of the forward and backward propagating fields at z=L:

$$c^{(b,L)} = R c^{(f,L)}, \quad (7)$$

with the matrix $R \in C^{N \times N}$ that describes all reflections for z≥L, including the fiber end face and any sample behind it. Hence, the coupling between forward and backward propagating fields takes place only for z≥L. For the following calibration procedure, the matrix R needs to be precisely known, regular, and it needs to have distinct singular values. According to Eq. (7), this regularity means that all forward propagating modes need to couple to all backward propagating modes. In other words, during the calibration procedure, any potential impact of a measuring sample (for z≥L) on the reflector matrix R must be precisely known and it must not impair the requirement that all backward modes receive a sufficient amount of light during the calibration, nor the distinctness of the singular values of R. In light of this requirement, it may be desirable to include a shutter or filter which blocks light from the sample during the calibration step. Since singular values are by definition real and nonnegative, they can only differ in modulus, but not in phase. The impact of noise on the distinctness condition would be minimized by maximizing the spacing between the singular values $D_{R,n,n}$ of R. In one embodiment, this is achieved by designing the reflector such that its singular values are equidistantly spaced. Since R needs to be regular, its singular values must be nonzero. Combining both conditions (distinctness and regularity), it is therefore desirable if, in mathematical terms, for every m=1, . . . , N, there is a unique n with 1≤n≤N such that the singular value $D_{R,n,n}$ satisfies the condition $$D_{R,n,n} = \frac{N-m}{N-1} D_{R,min} + \frac{m-1}{N-1} D_{R,max},$$

where we define the minimum and maximum singular values $D_{R,min} = \min_{n=1, \ldots, N} D_{R,n,n}$ and $D_{R,max} = \max_{n=1, \ldots, N} D_{R,n,n}$. The optimum value $D_{R,min}$ is a tradeoff between the noise sensitivity of the regularity condition and the noise sensitivity of the distinctness condition. The optimum value $D_{R,max}$ is a tradeoff between the noise sensitivity of the distinctness conditions, and the maximum allowed reflectivity (which may be up to 100% if, e.g., a shutter is being used). While such a perfectly equidistant distribution of singular values may be hard to fabricate, there are reflector designs that come close to such a distribution.

Combining Eqs. (7), (6) and (3), we obtain $$c^{(b,0)} = W^{(b)} R W^{(f)} c^{(f,0)}. \quad (8)$$

If the permittivity, permeability and conductivity (the latter being trivially zero at optical wavelengths) tensors of the waveguide materials are symmetric, the waveguide itself is reciprocal, i.e., we have the symmetry relation (the superscript "T" denotes the matrix transpose, without complex conjugation)

$$W^{(b)} = W^{(f)T}. \quad (9)$$

Inserting Eq. (9) in Eq. (8), we obtain $$c^{(b,0)} = W^{(f)T} R W^{(f)} c^{(f,0)}. \quad (10)$$

Repeating Eq. (10) for N input vectors $c^{(f,0)}$, we obtain $$C^{(b,0)} = W^{(f)T} R W^{(f)} C^{(f,0)}, \quad (11)$$

where each column of the matrix $C^{(f,0)} \in C^{N \times N}$ represents a proximal input vector $c^{(f,0)}$, and each column of the matrix $C^{(b,0)} \in C^{N \times N}$ represents a proximal output vector $c^{(b,0)}$.

Assuming that these N proximal input vectors $c^{(f,0)}$ are linearly independent, the inverse $C^{(f,0)-1}$ of the matrix $C^{(f,0)}$ exists, and Eq. (11) gives $$W^{(f)T} R W^{(f)} = C^{(b,0)} C^{(f,0)-1}. \quad (12)$$

For the following calibration procedure, $W^{(f)}$ (and thus $W^{(b)}$ according to Eq. (9)), need to be unitary matrices, i.e., $$W^{(f)H} = W^{(f)-1}, W^{(b)H} = W^{(b)-1}, \quad (13)$$

where the superscript "H" denotes complex conjugate transpose. Using the Euclidean norm, this implies $\|W^{(f)}\|_2 = \|W^{(b)}\|_2 = 1$, i.e., lossless propagation along the multimode waveguide.

If the permittivity, permeability and conductivity (the latter being trivially zero at optical wavelengths) tensors of the reflecting materials (including the sample) are symmetric, the reflector itself is reciprocal. In this case, we have the symmetry relation and Takagi factorization (which is well suited here because it uses a transposed (denoted by the superscript "T") instead of complex conjugate transpose or inverted matrix)

$$R = R^T = U_R^T D_R U_R, \quad (14)$$

with the diagonal matrix $D_R \in R^{N \times N}$ having non-negative entries, and the unitary matrix $U_R \in C^{N \times N}$ (note that the columns of $U_R$ are not the eigenvectors of R, as $D_R$ contains the nonnegative square roots of the eigenvalues of $RR^H$). Due to Eq. (14), the matrix $W^{(f)T} R W^{(f)} = C^{(b,0)} C^{(f,0)-1}$ in Eq. (12) is symmetric, i.e., $(W^{(f)T} R W^{(f)})^T = W^{(f)T} R W^{(f)}$ and we can therefore decompose it as well using a Takagi factorization $$U^T D U = C^{(b,0)} C^{(f,0)-1} = W^{(f)T} R W^{(f)} = W^{(f)T} U_R^T D_R U_R W^{(f)}, \quad (15)$$

with the diagonal matrix $D \in R^{N \times N}$ having non-negative entries, and the unitary matrix $U \in C^{N \times N}$. Based on the assumptions mentioned above (unitary waveguide matrix $W^{(f)}$, regular reflector matrix R and product matrix $C^{(b,0)} C^{(f,0)-1}$, distinct entries along the diagonal of $D_R$), Eq. (15) implies $$\sqrt{D} D_s U = \sqrt{D_R} U_R W^{(f)}, \quad (16)$$

with an unknown diagonal matrix $D_s \in R^{N \times N}$ having elements 1 and −1 on its diagonal. Thus, Eq. (16) is equivalent to $$W^{(f)} = U_R^{-1} \sqrt{D_R^{-1} D} D_s U. \quad (17)$$

In other words, even if we know the mode coefficients matrix product $C^{(b,0)} C^{(f,0)-1}$ and the entire diagonalization Eq. (14) of the reflector matrix R, a diagonal matrix $D_s$ containing N unknown signs is still missing from a complete knowledge of the waveguide forward propagation matrix $W^{(f)}$. This is due to the fact that the forward propagating (input) field at the proximal end z=0 has to travel twice through the waveguide to become the backward propagating (output) field at the proximal end z=0. However, to scan a sample at the distal end, exact knowledge of the single pass transfer function $W^{(f)}$ is necessary.

Thus, a method to determine the signs of the N diagonal entries of the matrix $D_s$ in Eq. (17) is required. In one embodiment, these entries may be determined using a proximally controlled distal source. This distal source has an E-field for which we know the modal coefficient vector $c^{(b,L)} = c_s^{(b,L)}$ in Eq. (6). We describe further of how these coefficients may be determined. Once these are known, we may relate $c_s^{(b,L)}$ to the modal coefficient vector $c_s^{(b,0)}$ observed at the proximal end using Eqs. (17) and (10):

$$c_s^{(b,0)} = W^{(f)T} c_s^{(b,L)} = U^T D_s \sqrt{D_r^{-1} D} U_R^{T-1} c_s^{(b,L)}. \quad (18)$$

Here we have included the round trip calibration from Eq. (17), which includes the indeterminate matrix $D_s$.

We now use Eq. (18) to determine $D_s$ from the distal source modal coefficients $c_s^{(b,L)}$ and from the resulting proximal modal source coefficients $c_s^{(b,0)}$ measured after propagation of the distal source E-field from the distal to the proximal end of the imaging waveguide. Since the complex conjugate (denoted by the asterisk superscript "*") of a unitary matrix is equal to the inverse of its transpose, we have $U_R^{T-1} = U_R^*$ and $U^{T-1} = U^*$. Hence, Eq. (18) is equivalent to $$U^* c_s^{(b,0)} = D_s \sqrt{D_R^{-1} D} U_R^* c_s^{(b,L)}. \quad (19)$$

Defining in Eq. (19) the left hand side vector $a = U^* c_s^{(b,0)}$ and the right hand side vector $b = \sqrt{D_R^{-1} D} U_R^* c_s^{(b,L)}$, we obtain the set of N scalar decoupled equations $a_n = D_{s,n,n} b_n$, because $D_s$ is a diagonal matrix. Since these unknown entries $D_{s,n,n}$ on the main diagonal of the matrix $D_s$ can only be +1 or −1 as stated below Eq. (16), they can be determined from the following equation:

$$D_{s,n,n} = \text{sgn}(\text{Real}(a_n b_n^*)), a = U^* c_s^{(b,0)}, b = \sqrt{D_r^{-1} D} U_r^* c_s^{(b,L)}. \quad (20)$$

Figure 12:
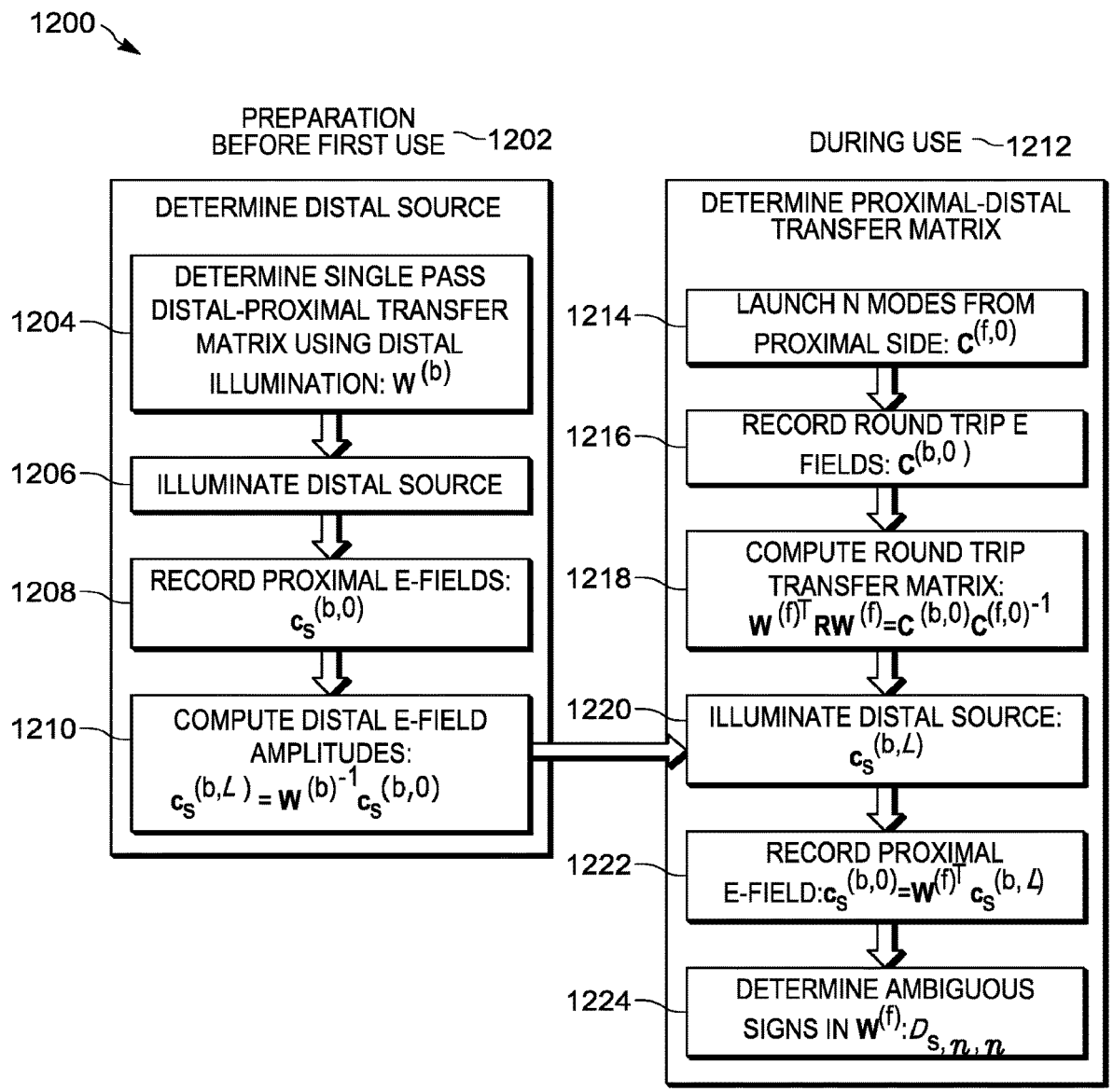
FIG. 12 illustrates a flow chart showing an embodiment of a method of imaging waveguide calibration according to the present teaching.

FIG. 12 shows a flow chart of the steps for preparation before first use including determining the distal source amplitudes $c_s^{(b,L)}$. Eq. (20) can be used to correctly compute the previously unknown signs in the diagonal matrix $D_s$ in the calibration Eq. (17) derived from round trip calibration measurements. The signs may be determined as long as all elements of the proximal output $c_s^{(b,0)}$ and distal input $c_s^{(b,L)}$ have a sufficiently large modulus and if noise in the system does not flip the signs of any of the products $a_n b_n^*$ in Eq. (20). If any of the values of $a_n b_n^*$ are below the noise level and thus, susceptible to errors in the determination of their sign, it is possible to include one or more additional distal sources for which these values are sufficiently large that they are not affected by noise.

If the reflector is not reciprocal, e.g., due to a significant magneto-optic effect, the matrix R in Eq. (12) is not symmetric and we cannot use a Takagi factorization as in Eq.

(14). Hence, Eqs. (14) to (20) are not valid in this case of a non-reciprocal reflector. Instead, we use a more general singular value decomposition $$R = U_R^T D_R V_R, \tag{21}$$

with the diagonal matrix $D_R \in R^{N \times N}$ containing the nonnegative singular values of the matrix R, and the unitary matrices $U_R, V_R \in C^{N \times N}$. We note that Eq. (21) is notationally analogous to Eq. (14), and mathematically equivalent to the more common convention $R = U'_R D_R V'^H_R$ with the unitary matrices $U'_R = U_R^T$ and $V'_R = V_R^H$. Inserting Eq. (21) in Eq. (12), a singular value decomposition of $C^{(b,0)} C^{(f,0)^{-1}}$ gives $$U^T D V = C^{(b,0)} C^{(f,0)^{-1}} = W^{(f)T} R W^{(f)} = W^{(f)T} U_R^T D_R V_R W^{(f)}, \tag{22}$$

with the unitary matrices U, $V \in C^{N \times N}$ and the diagonal matrix $D \in R^{N \times N}$ containing the nonnegative singular values of the matrix $C^{(b,0)} C^{(f,0)^{-1}}$. If the waveguide matrix $W^{(f)}$ is unitary, the products $W^{(f)T} U_R^T$ and $V_R W^{(f)}$ are unitary as well, so the right hand side of Eq. (22) can still be interpreted as a singular value decomposition. If both sets of singular values, i.e., the entries along the diagonals of the matrices D and $D_R$, are sorted in nonincreasing order, they are unique, i.e., we have $D = D_R$. Furthermore, if all singular values in matrix D (or $D_R$, respectively), are distinct, Eq. (22) implies $$D_c^* U = U_R W^{(f)}, \quad D_c V = V_R W^{(f)}, \tag{23}$$

with a diagonal matrix $D_c \in C^{N \times N}$ having entries of unit modulus $|D_{c,n,n}| = 1$ on its diagonal for all n=1, . . . , N. Eq. (23) can be interpreted as an iterative procedure to determine the single pass propagation matrix $W^{(f)}$ and the diagonal matrix $D_c$ containing the unknown complex phases, without need for an additional condition such as a distal source. However, in contrast to the symmetric case from Eqs. (15) and (20), there is no sign function involved that would give an exact result even in presence of moderate noise. Nevertheless, even in the case of a nonreciprocal reflector, the impact of noise on the distinctness of its singular values can be minimized by using a reflector design with equidistant or approximately equidistant singular values, see the discussion above Eq. (8).

One feature of the present teaching is that a distal source can be utilized that is controlled at the proximal end of the probe. This distal source has several properties in various embodiments. First, the distal source is controlled only by proximal optics and electronics, as needed. The controlled parameters can include the wavelength, power, phase, and state of polarization. Any or all of these parameters may be modulated as a function of time, or scanned over ranges, or varied among a set of discrete states. Second, once illuminated by the proximal optics, the distal source does not change significantly as the multimode waveguide experiences bends, and other perturbations. In some embodiments, any change in the distal source is designed to be sufficiently small so that it can still be used to provide a calibration of the multimode waveguide. In some embodiments, the calibration of the multimode waveguide allows for the formation of a focus at the end of the fiber that can be used for a medical procedure, including imaging, OCT, fluorescence, confocal optics and laser power delivery. In some embodiments, the calibration also allows for the scanning of the focal spot over a range of positions. If the calibration is not perfect, then the desired transverse field pattern (e.g., a spot) will be accompanied by light that is typically unfocused and adds noise, and thus degrades the desired imaging or laser delivery application. In general, such applications will be tolerant to a certain spot distortion and signal-to-noise level.

A useful calibration provides a formulated spot with sufficient performance in various parameters to provide a successful probe measurement. For example, in some embodiments, the calibration will allow formation of a spot that generates distortion and noise at a level that is below the acceptable level required for an imaging or a laser delivery application.

A third property of the distal source is that it can excite a sufficient number of the multimode waveguide's modes that $D_{s,n,n}$ can be determined. A fourth property of the distal source is that the distal source interferes only minimally with the imaging signals from the sample that must propagate in the imaging waveguide. For instance, during the imaging process (after calibration), all signals from the distal source that might be excited by the light used for imaging, could be much less than 1% of the imaging signals. In some embodiments, the fraction of power from the distal source that reaches the proximal processing detectors is low enough to ensure it is <1%, or some other sufficient level, of the power from the imaging signal that reaches the proximal processing detectors. In some embodiments, the one or more distal source light is gated and/or filtered to reduce the effects of the one or more distal sources interfering with measurement light generated by the sample. The gating may be provided using coherence, time, wavelength, or other types of gating or filtering. It is also possible to electro-optically or physically remove and replace the reflector during the sample measurements. The distal source may also be at a wavelength separated from the imaging wavelength range, but still close enough to be useful.

Figure 6A:
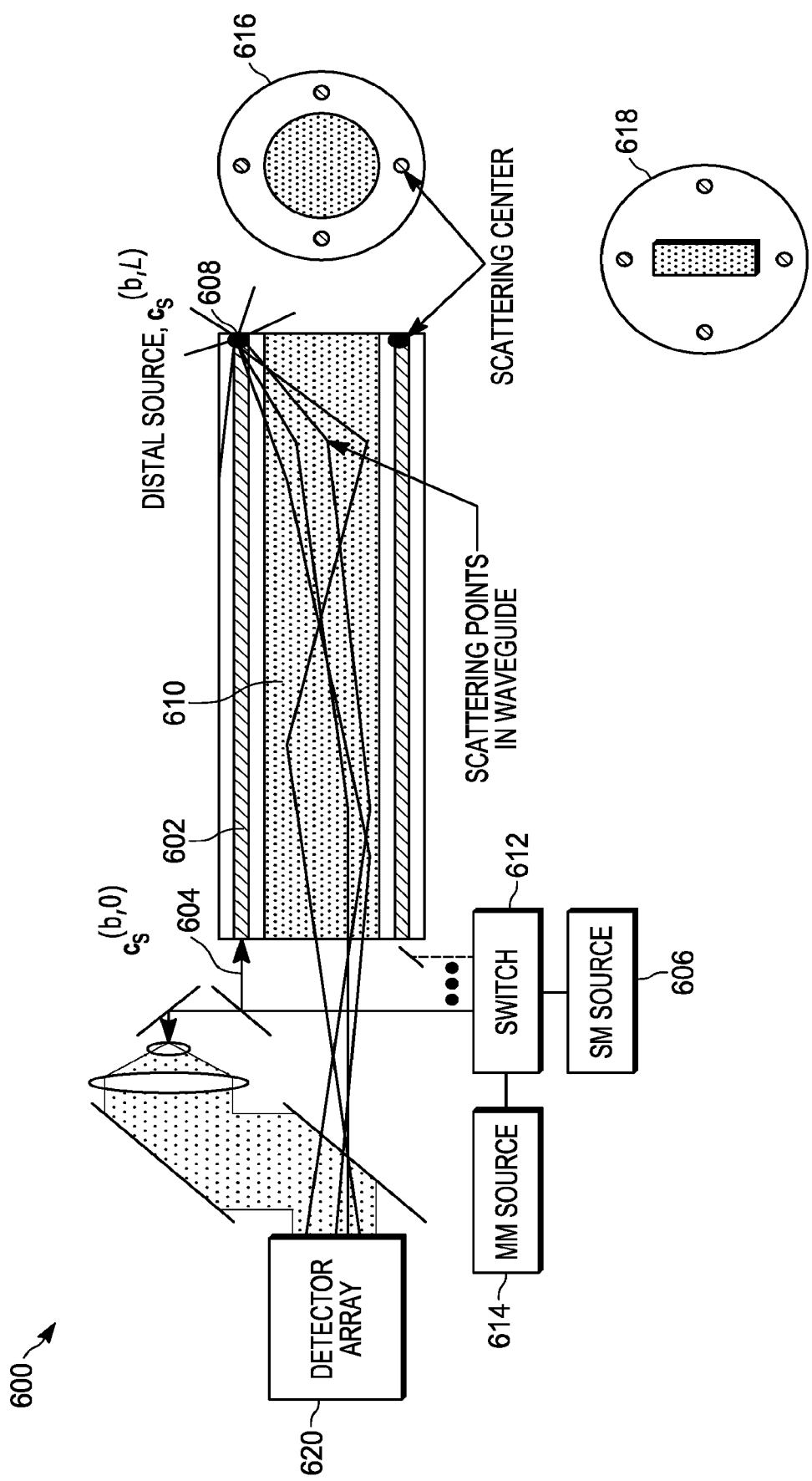
FIG. 6A shows an embodiment of a remote optical probe system of the present teaching comprising a single mode or few-mode waveguide that carries light to a scattering center at the end of the fiber.
Figure 6B:
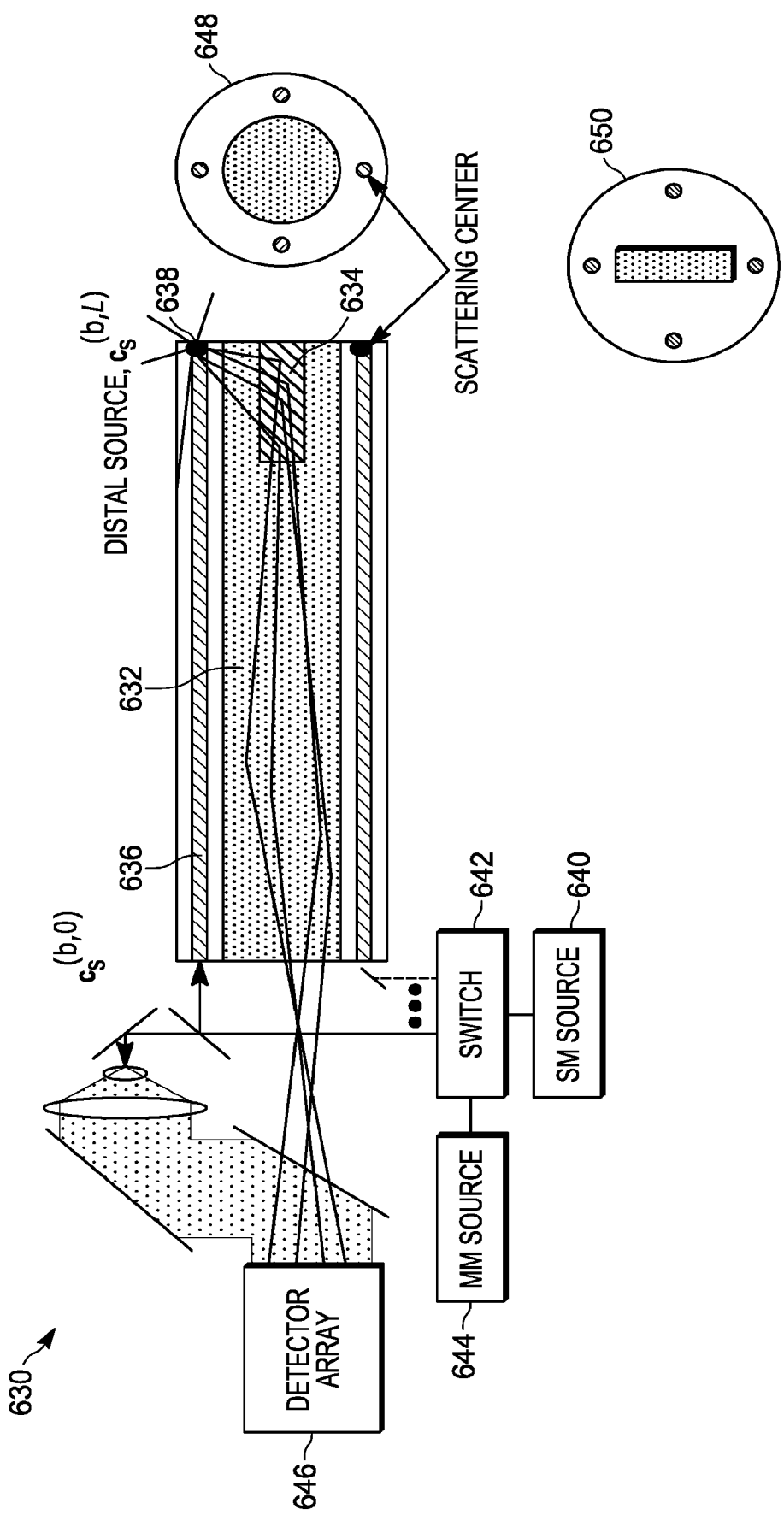
FIG. 6B shows an embodiment of a remote optical probe system of the present teaching comprising additional scattering centers introduced into the imaging waveguide.
Figure 6C:
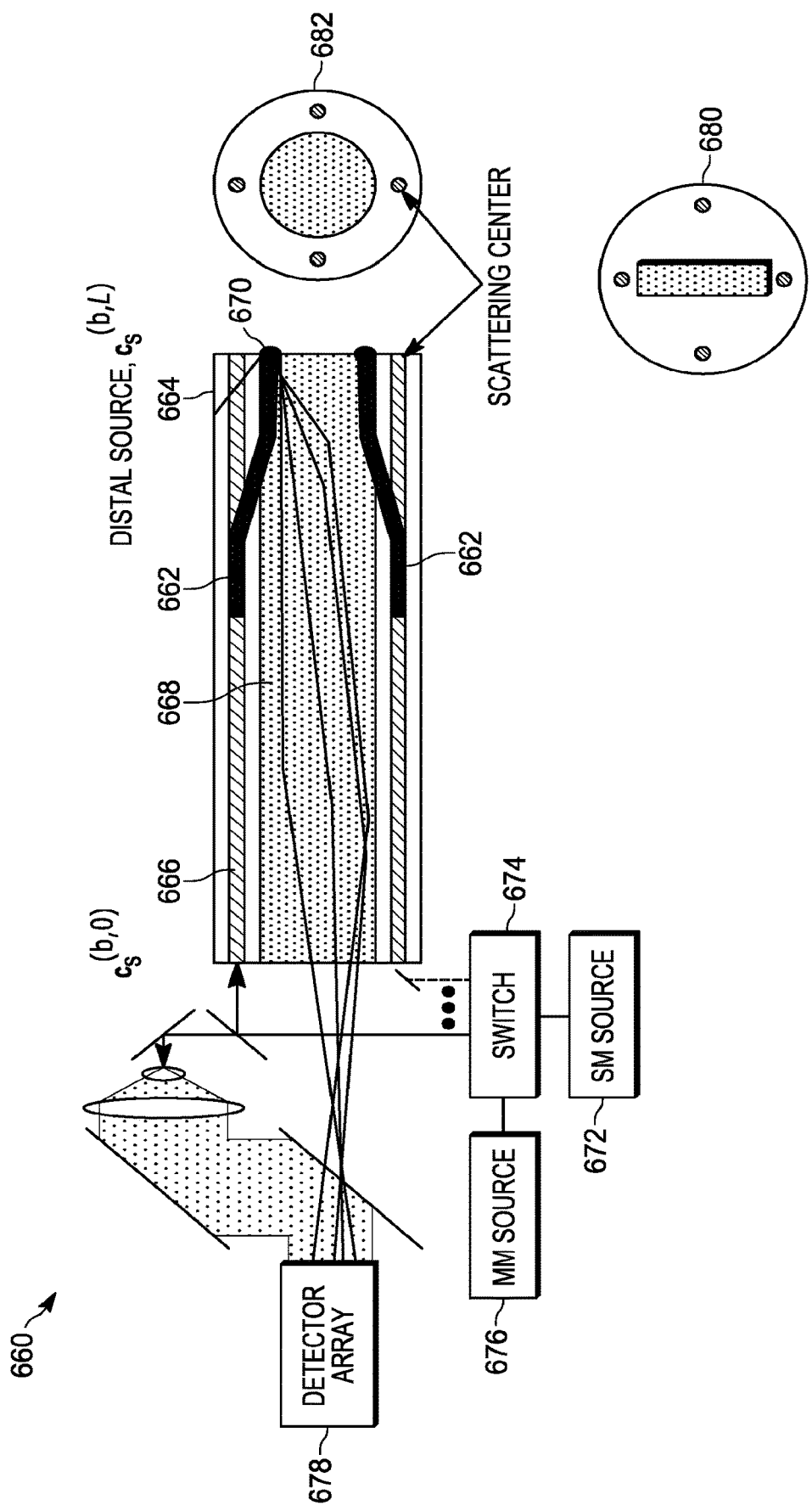
FIG. 6C shows an embodiment of a remote optical probe system of the present teaching comprising a single mode coupling waveguide that is made to overlap with the imaging waveguide.

FIGS. 6A-D illustrate example concepts of a multicore waveguide containing a multimode core and single mode fibers to create a distal source. Each figure shows how a proximally controlled distal source may be coupled to a multimode imaging waveguide. Note in FIGS. 6A-D, the single mode source (e.g. single mode source 606) can be a source that has a fixed spatial profile, for example, a beam from a single-mode fiber or single-mode laser. This single-mode source is coupled to the distal sources (e.g. single mode source 608). The multi-mode source (e.g. multimode source 614) can be a beam that has a more complex cross sectional spatial profile and, for example, can be a light signal or light beam originating from the single mode source and propagated to, and altered by, a spatial light modulator. In many embodiments, the light from this multimode source is then propagated and coupled into the proximal end of the imaging waveguide (even though the embodiments shown in FIGS. 6A-6D do not illustrate this particular step of coupling the multimode source into the imaging fiber). The distal illumination resolves the sign ambiguity of a single pass transfer function from a round trip calibration. FIGS. 6A-C do not show the round trip calibration procedure. Examples of circular cores and rectangular cores (that could be used for one dimensional operation) are shown. The proximally controlled distal source may be realized in many ways. FIG. 6A illustrates a probe system 600 that includes a waveguide 602 that carries light 604 generated by a single mode source 606 to a distal source 608 at the end of the waveguide 602. The distal source may take the form of a scattering center at the end of the waveguide 602. The waveguide 602 may be a single mode or few-mode waveguide. In a preferred embodiment, the waveguide 602 is a single mode waveguide. In this way, any bend, twist, thermal variation or other perturbation of the overall waveguide will have no effect on the distal source. Only the phase will change. Such an overall phase change will not be important in the calibration procedure. However, a single mode waveguide may also support two orthogonal polarizations. If the polarization variation along a single mode waveguide is too large for the distal source to have a constant polarization, then it is possible for the single mode waveguide 602 to be a polarization maintaining waveguide or to include polarizing components along the path. It is also possible for the single mode waveguide 602 to be a polarizing waveguide, for which only a single polarized mode can propagate. The waveguide 602 is proximate to a multimode imaging waveguide 610. In one embodiment, scattering within the imaging waveguide 610 would ensure that some of the light scattered by the scattering center 608 would be coupled into the imaging waveguide 610. There may be an optional switch 612 if more than one distal source is to be utilized. Optionally, a multimode source 614 may also be connected through the switch 612. In some embodiments, the same single mode source 606 could feed the multimode source 614. The multimode waveguide cross sections 616, 618 of FIG. 6A also illustrate how different waveguide geometries can be utilized. For example, the circularly symmetric cores of cross-section 616 are suitable for 2D imaging. The more rectangular cores of cross section 618 are suitable for either 1D or 2D imaging. A detector array 620 at the proximal end receives light from the single mode source 606, as well as the scattered light from the multimode waveguide 610 and sends the detected signal information to a processor (not shown) that performs the calibration steps described above. The detector and processor may also perform the imaging or other measurement steps of the probe system from measurement light collected by the multimode waveguide from a sample and propagated back to the detector by the multimode waveguide.

FIG. 6B shows an embodiment of a system 630 of the present teaching comprising additional scattering centers that are introduced into the imaging waveguide 632. The scattering center 634 is located at the distal end of the imaging waveguide 632. These scattering centers couple a portion of the light scattered from the single mode waveguide 636 into a well-defined light 638 within the imaging waveguide. In one embodiment, these scattering centers form a periodic structure that phase matches the light scattered from the single mode waveguide. The dimension of this grating may be designed to give a certain distal source spot size. The grating planes may be blazed to increase coupling from scattering out of a given single mode waveguide. The system of FIG. 6B includes a single mode laser source 640, switch 642, multimode laser source 644, and detector array 646 similar to the probe system described in connection with FIG. 6A. FIG. 6B also illustrates in cross section 648, that the multimode waveguide in some embodiments can have a circular shape. The cross section 650 illustrates a rectangular shaped multimode waveguide in some embodiments.

FIG. 6C shows an embodiment of a remote optical probe system 660 of the present teaching comprising a single mode (or few-mode) coupling waveguide that is made to overlap with the imaging waveguide. One or more coupling waveguides 662 are formed in a multicore fiber 664. Such a coupling waveguide 662 could be written using actinic radiation, such as UV, or IR femtosecond radiation. The actinic radiation could change the refractive index sufficiently that a portion of the light in the single mode waveguide 666 would be coupled to the coupling waveguide 662. This coupling waveguide 662 could then be made to overlap with the imaging waveguide 668. A scattering center 670 in the imaging waveguide 668 would then provide the required distal source. Alternatively in some embodiments, instead of a coupling waveguide 662, it is also possible to taper the entire multicore fiber 664. With a sufficient taper, the E field in the single mode waveguide 666 would overlap with the imaging waveguide 668, resulting in coupling. Scattering or reflection of light in the imaging waveguide 668 would then give a distal source. The system of FIG. 6C includes a single mode source 672, switch 674, multimode source 676, and detector array 678 similar to the probe system embodiments of FIGS. 6A-B. FIG. 6C also illustrates in cross section 680 that the multimode waveguide used in some embodiments may have a rectangular shape. The cross section 682 illustrates a circular shaped multimode waveguide that is used in some embodiments.

In various embodiments, the scattering center(s) converts the single mode light into many modes, at least some of which propagate in the multimode waveguide back toward the proximal end. One way to accomplish such scattering is to introduce one or more index perturbations into the distal end of the waveguide to reflect or scatter light. These may be, for instance, index perturbations created using actinic radiation, holograms, gratings, discrete scattering centers such as voids introduced, for example, using femtosecond laser pulses. A sufficient number of such perturbations can create a stable source that excites many modes at the distal end. In some embodiments, there are small index perturbations in the imaging waveguide to capture the scattered light, as indicated in FIGS. 6A-B. This might be required if the transverse position of the single mode waveguide was offset from the center of the imaging waveguide to such an extent that scattering from the single mode waveguide would not be well captured in the imaging waveguide.

Figure 6D:
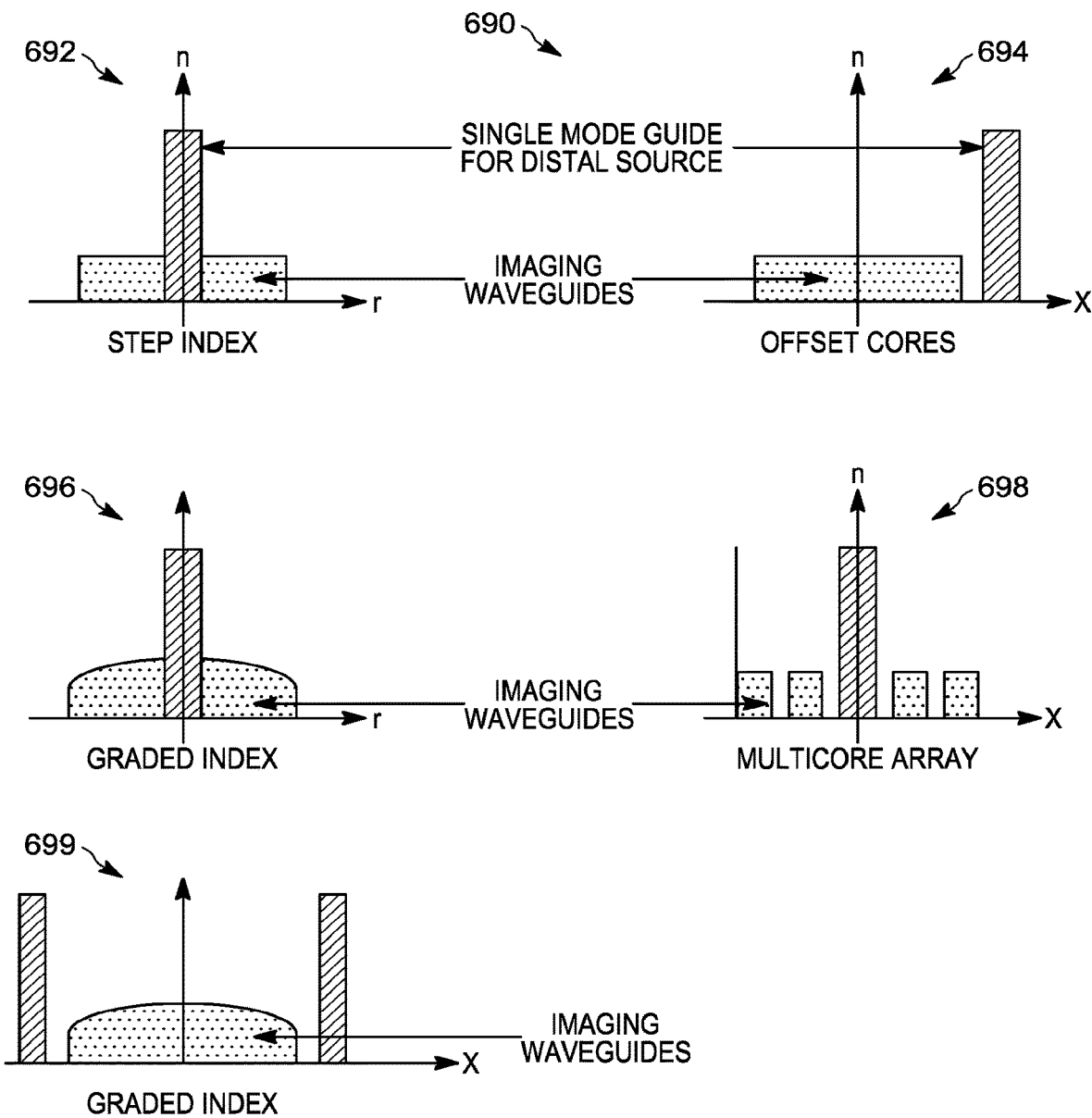
FIG. 6D illustrates refractive index profiles of both the imaging waveguides and the distal source waveguides of example embodiments of the remote optical probe system of the present teaching.

FIG. 6D illustrates a set of five example refractive index profiles 690 of both the imaging waveguides and the distal source waveguides representing four example embodiments of the remote optical probe system of the present teaching. Possible imaging waveguides include step index 692, offset cores 694, graded index 696, and multicore 698, and graded-index multimode fiber with offset single-mode (or few mode fibers) 699. The profiles are presented as refractive index, n, as a function of radius, r, or x-axis, x, from the center of the fiber. More complicated refractive index profiles, such as profiles that include trenches or pedestals, are possible as well. The distal source waveguide may be within the imaging waveguide or it may be offset from it. When the distal source waveguide is within the imaging waveguide, it is preferred that the raised index region defining the distal source waveguide supports only a single mode that has very little coupling with the many modes in the surrounding imaging waveguide.

In some embodiments, light from the single mode waveguide may be fully or partially focused onto a scattering region just beyond the end of the fiber (e.g. within a protective cap of the endoscope) or even at the fiber facet itself. In one embodiment, this focal region may be made very similar to the desired focal spot used in the imaging application.

In some embodiments, the distal source could be formed within the sample itself For instance, a single mode waveguide could be combined with the multimode waveguide. It might, for instance, be at the center of the multimode waveguide. For instance, an additional refractive index step above the index step forming the multimode waveguide could provide such a single mode waveguide. The mode guided in such an additional index step would have to be sufficiently decoupled from the other modes of the imaging guide that light could propagate in this core without coupling to the other modes. Thus, although the overall waveguide would support many modes, the additional index step would allow for effective single mode guidance over the length of the fiber. Light from this single mode waveguide would then be focused onto the sample to form the distal source and then OCT could be used to form an image along the axis of this focus. Thus, there could be several distal sources along the axis of the focal spot, giving rise to the distal source scattering. Simultaneously, the imaging waveguide would collect light from the same focal spot. The same OCT processing would be performed on these multimode imaging fiber signals to obtain the signal from the focal spot or spots. We note that because the OCT processing yields axial and wavelength dependent information, this information could also be used to calibrate the wavelength dependence of the waveguide. In order to scan the beam at the distal end, the light would be launched from the proximal side with a linear transformation on the proximal light that corresponds to a translation of the beam at the distal end. That is a spatial amplitude and phase profile would be applied to the optical beam before it is coupled into the multimode waveguide that serves to translate the optical beam at the distal end.

In some embodiments of the apparatus of the present teaching, the focal spot would not be in the sample. Instead it would be on a known region in the vicinity of the source.

Also, in some embodiments of the apparatus of the present teaching, a beam splitter and two shutters are included. When shutter 1 is closed, the light leads to a distal source for calibration. Once that calibration is complete, shutter 1 is opened and leads the light to the sample and shutter 2 is closed blocking light from the calibration.

One skilled in the art will appreciate that there are various types of light described in some embodiments of the present teaching. These types of light include, light reflected from the distal target, R, light from the distal calibration lights, and light from the sample. It is noteworthy that the multiple types of light can be detected separately in time through a combination of modulating various sources of the light and/or the use of opening/closing shutters. But, it is also possible to detect one or more of the multiple types of light in parallel using gating techniques, such as wavelength separation and filtering, modulation separation (e.g., imparting modulation and detecting at different electrical frequencies or codes), coherence gating, polarization gating, and other approaches.

In some embodiments, the distal source may be a fluorescent material that is, for example, coated on, or embedded in, the end of the fiber. When irradiated with a pump wavelength, this source would provide fluorescence at the desired wavelength and may contain a spatial pattern determined by the placement of the fluorescent material. The pump wavelength may be outside the wavelength range of the imaging system and/or detector arrays at the proximal end of the system.

In some embodiments, the single mode distal source is only turned on periodically at the end of an imaging sweep, during which time the multimode optical excitation is turned off.

In some embodiments, the distal source may be formed by reflecting the light from the single mode waveguide by roughly 90 degrees so that it propagates across the distal face of the imaging waveguide. Surface features at this distal face would then scatter light back into the imaging waveguide. It is also possible that the reflected light could be reflected at even more than 90 degrees using various optical components, for example, small reflective prism mirrors.

In some embodiments, the single mode waveguide would be at the edge of the multimode waveguide and slightly overlapping it. Any scattering from such a single mode waveguide would then be captured in the multimode waveguide without the requirement for additional scattering within the waveguide. Moreover, such a single mode waveguide would be sufficiently far away from the center of the imaging waveguide that it would have very little impact on image quality. Note that many such single mode waveguides that are at the periphery of the imaging waveguide can be used.

In some embodiments of the apparatus of the present teaching, a ring of high refractive index material surrounds the imaging waveguide with possibly some optional overlap. Stable orbital angular momentum modes could then be excited in such a ring in place of the single mode waveguide modes.

In various embodiments, it is important that the optical modifications at the distal end face that are required to produce the distal source have minimal impact on the imaging light that propagates through the imaging waveguide during the imaging process. This distal source would usually not be illuminated during the imaging process, since it is only required for calibration. A possible exception is the case that the wavelength range of the distal source is disjoint from the wavelength range that is used for imaging. In this case, the distal source could operate simultaneously with the imaging process. If both wavelength ranges overlap or are identical, it may be possible that the modifications to the overall waveguide, which are required to give rise to the distal source, might interfere with the imaging process by producing unwanted signals. These signals must be negligible in comparison to the imaging signals. Thus, for instance, the fraction of power scattered by the distal source optics should be less than 1% of the expected signal power from the sample to be imaged when the imaging illumination is turned on. For instance, in some OCT imaging arrangements, the scattered power is 110 dB lower than the incident power. In this case, the optical modifications giving rise to the distal sources should generate less than −130 dB. There can be other techniques used to compensate and separate the unwanted scattering from distal source optics (e.g., if. filtering). Thus, in any imaging application, the distal source optics would modify or degrade the image by a small amount (e.g. less than 1%).

It is understood that it may be necessary to use much larger power to excite the distal source in order to overcome the small scattering fraction that couples the distal source into the imaging waveguide. It is also understood that most of this light would be either absorbed or reflected and would not be allowed to enter a sample if that sample were sensitive to such radiation. In one embodiment, the distal source light is from a wavelength stabilized narrow linewidth laser and is separated from the other light used for imaging using proximal optical filtering. This approach comes at additional proximal processing complexity. Alternatively, methods can also be used to separate the three most important types of light in the present teaching, light that was reflected by the sample, light that was reflected by the reference reflector, and light from the distal source. These methods include, for example, coherent gating, time gating, operating an optical shutter, and physical removal of the endoscope from the sample.

In some embodiments of the apparatus of the present teaching, the distal source is generated using any of a number of methods, such as reflection, scattering, fluorescence. The distal source may have any wavelength, though wavelengths within the signal bandwidth are desirable for some applications.

In some embodiments of the apparatus of the present teaching, the distal source is generated sufficiently close to the distal end of the fiber and the imaging volume such that fluctuations of phase, amplitude or polarization between the distal source, any remaining fiber, and the sample to be imaged do not cause unacceptable loss of calibration or other degradation of the image. That is, a distance of the distal source from the end of the fiber is chosen such that light from the distal source does not cause degradation of the image or loss of calibration of the system.

One skilled in the art will appreciate that the location and character of the distal source should be such that the optical properties of the imaging light remain deterministic and stable between the distal source and the image volume. In general, the location of the distal source may not be exactly the same as the location of the volume to be imaged. Therefore, an additional transformation, as is known in the art (e.g., Rayleigh-Sommerfeld, Fresnel, Fraunhofer, or similar deterministic propagation), would be implemented to convert the mode fields from the distal end of the fiber to the desired light shape and position of the volume to be imaged. For instance, there might be many millimeters or even centimeters of optical path separating the distal source and the imaging volume.

The input signal light may be adjusted to produce desired characteristics at the distal source. The adjustments include fiber illumination position and/or phase and/or amplitude of the input signal light. For example, if light from multiple cores illuminates a small bubble at the distal end, light will be scattered back into each of the cores. The characteristics of the input light may be manipulated to control the amount of light scattered back into one specific core. Referring back to FIG. 6A, the direction of light propagating in the fiber can be reversed from that shown in the figure so that multimode light launched into the proximal end of the multimode waveguide 610 is focused onto the distal source 608, which then reflects light back along the single mode waveguide 602.

In some embodiments of the apparatus of the present teaching, tip shaping at the distal end of the fiber may be used to steer the beam or modify the scanning range and resolution. The shape of the tip may be such that one or more spots are produced simultaneously to image the sample.

In some embodiments, it is possible to avoid the limitations of both the distal source and/or the initial calibration by incorporating shape sensing into the imaging fiber. In these embodiments, the shape of the multimode imaging fiber is determined. One way to determine the shape of the fiber is by adding additional single mode cores and using the back scatter from these cores to reconstruct the shape of the fiber. Such cores could also be used to obtain the temperature and axial strain distribution along the fiber. This shape, temperature, and axial strain information could then be used to compute the transfer matrix for the imaging waveguide in a manner known in the art. The value of the transfer matrix obtained in one of these manners known in the art could also be used to compute $D_{s,n,n}$ as in the analysis presented above. That is, the transfer matrix computed from the fiber shape could be used instead of, or in addition to, an initial calibration or instead of, or in addition to, the use of a distal source. In methods that use known methods to determine a shape of the fiber, it would not be necessary to determine the transfer matrix beforehand, and not necessary to use a distal source. Moreover, the uncertainty associated with relying on an initial calibration would be removed. In some embodiments, a distal source could also be used, in addition to the shape sensing capability. Such a distal source would be easily implemented since the shape sensing would require single-mode cores in the fiber, and one or more of these single-mode cores could be used to supply light to a distal source. The shape of the fiber may be determined by including three or more single mode cores as described in, for example, Jason P. Moore and Matthew D. Rogge, "Shape Sensing Using Multi-Core Fiber Optic Cable and Parametric Curve Solutions", Optics Express, Vol. 20, Issue 3, pp. 2967-2973, https://doi.org/10.1364/OE.20.002967, 2012, which is incorporated herein by reference. This reference describes that light scattering from such single mode cores in a multi-core fiber can be used to yield the shape of the fiber.

In some embodiments of the apparatus of the present teaching, a multimode imaging core could have within it, and/or outside of it, one or more single mode fiber cores. These single mode cores could be used to obtain the local strain and temperature distributions within the multimode fiber and thereby allow for a continuous calibration of the imaging fiber. One way to obtain such data would be to perform swept wavelength interferometry on back scattered light from these cores. Back scattered light could be generated through Rayleigh scattering or through the introduction of scattering centers via, for example, UV inscribed intracore Bragg gratings. See, for example, Paul S. Westbrook, Tristan Kremp, Kenneth S. Feder, Wing Ko, Eric. M. Monberg, Hongchao Wu, Debra A. Simoff, Thierry F. Taunay, Roy. M. Ortiz, "Continuous multicore optical fiber grating arrays for distributed sensing applications", Journal of Lightwave Technology, v PP, Issue 99, pp 1-5, doi:10.1109/JLT.2017.2661680, 2017, which in incorporated herein by reference and references therein.

In some embodiments, the various required modes could be launched into the imaging fiber using a photonic lantern. Excitation of multiple modes in a multimode waveguide using a photonic lantern allows each mode to be controlled independently as the lantern excites a specific mode in the waveguide. A photonic lantern can have many single mode cores on one end which could be used to launch the light using only single mode launch optics. The number of modes that could be launched would depend on the number of cores in the photonic lantern. A tapered region converts the various single mode launched beams into the desired multiple modes required to reconstruct a given pattern at the distal end of the fiber. The tapered conversion region could be close to or at the distal end, the proximal end, or somewhere in between.

Time gating and/or swept wavelength interferometry could be used to separate the calibrating signals obtained from various locations. For example, light sourced from the distal source, light sourced from the distal fiber reference target reflection used for round trip calibration, and light sourced from signals originating in the sample can be separated from each other and processed separately. These separation techniques can take many known forms, including optical and/or electrical light separation methods. In various embodiments, the light from these light sources may be referred to, individually or collectively, as calibration light. That is, light used for calibration may come from one or more sources and may be processed individually or separately.

In some embodiments, a non-scattering fiber end cap that protects the reflector and separates it from the sample would enable such a separation of calibration and signal data if a gating techniques was used (e.g. time, wavelengths, polarization, etc.). This alleviates the requirement for a shutter. In some embodiment of this method, a reference E field may be required for every detector at the proximal side. The reference E field would allow for swept wavelength interferometry to be performed at each pixel. Alternatively, time domain measurements can be performed.

The present teaching does not necessarily require that the sample is scanned by moving a focused spot. Instead, any other suitable set of linear combinations of the N modes of the multimode waveguide can be used for the imaging process if the detector can measure the optical phase across the transverse plane. This may be referred to as synthetic scanning, and the set of linear combinations may be chosen such that it spans the same space as the original N modes. In this way, the calibration and the imaging could be done with a single scan. Phase sensitive detection is used at the proximal side.

In some embodiments of the apparatus of the present teaching, the imaging waveguide could be pixelated with many coupled or uncoupled single mode cores. Such a pixelated fiber would have better control over mode coupling compared to a single multimode waveguide. In the limiting case, uncoupled cores may be excited individually such as by scanning a proximal source across each core and varying optical properties for each core independently as the source is scanned. If the cores are uncoupled, the transfer function is easily determined and calibration is simple, though at the expense of more complex proximal illumination and more stringent waveguide design. For example, optically uncoupled cores require a minimum degree of spatial separation, increasing the fiber size and creating unusable cross-sectional area which will degrade image quality and resolution. As the amount of mode coupling among cores increases, so does the computational complexity in determining the transfer matrix. There is a tradeoff between fiber complexity and system complexity and image quality. Mode coupling will depend on effective indices of the cores, which in turn, depends on the optical properties of each core and surrounding cladding (dimensions, refractive indices) and the relationship to surrounding cores. For example, coupling can be inhibited by increasing the separation in either physical distance or effective index between adjacent cores, such as by varying the core spacing, index or dimension or by adding lossy materials. It should be noted that the effective index differences between cores can depend on strain, bending and twisting.

One feature of the apparatus of the present teaching is that light can be launched into the multimode waveguide using several methods. General approaches that allow for arbitrary amplitude and phase (and optionally wavelength or polarization) across the multimode waveguide input facet exist including the general class of spatial light modulators (SLM), liquid crystal arrays, LCOS, MEMS, integrated photonic arrays, and photonic lanterns. For example, referring back to FIG. 4, a control device 412 can be used to provide the optical beam generated by the laser source 402 with a phase and/or amplitude modulation that is arbitrary within the resolution limit of the employed method (SLM etc.).

For some applications, it is not necessary to implement arbitrary amplitude and phase distribution at the fiber input facet. As such, it is possible to simplify the apparatus and to reduce the throughput loss. In such embodiments, it is possible to reduce laser-light-to-tissue throughput loss for maximum tissue signal to noise ratio (SNR) and also to minimize any system complexity. As such, "phase only" masks are sometimes desirable to use as a control device for generating the desired optical signal at the fiber input facet. One approach, which is suitable for synthetic scanning, is to use an angular scan mirror (e.g. galvo) or a simple phase-only spatial light modulator, to scan a focal spot across the fiber input facet located in the focal plane. Another approach is a dual approach that angularly scans across the fiber input facet with full aperture illumination with the fiber input facet in a pupil plane. At each fiber input launch, the wavelength is scanned. If only a single wavelength or a narrow wavelength range is used, the wavelength scanning step can be skipped. It is noted that the embodiments that use simple scanning mirrors cannot deliver arbitrary light to the input facet of the multimode fiber. However, these and similar approaches can be useful in obtaining the multimode fiber transfer function. Embodiments that use simple scanning mirrors are also useful for synthetic imaging approaches and other applications, as discussed later. It can be beneficial to minimize any unwanted fiber input facet or other stray reflections by anti-reflectance coatings or by using angle fiber facets. In some embodiments, it is possible to utilize the input facet reflection to confirm/measure/record the input field distribution.

At the distal end, straightforward methods exist to separate the reference reflection from the sample reflection. For example, coherence gating, wavelength separation, time gating, and the use of shutters can be used to separate the sample reflected light from the distal reference target light in the determination of the fiber transfer function. The shutter may be located in the distal optics module. Also, a multi-step process can be used where the light from the distal source, distal reference target, and sample are separated in time. This can be achieved by using shutters, modulating the multimode source and the single-mode source, or other means, during the calibration step.

One feature of the present teaching is that compensation of the optical fiber transfer function can be used to effectively deliver light with desired characteristics to a sample and/or to generate an image of a sample. This can be accomplished by determining the transfer function of the optical fiber and by using it to manipulate the optical field, either physically or in a digital or analog representation, in anticipation of being transformed, or after it has been transformed, by propagation through the optical fiber. The transfer function may be determined mathematically using calibration, as described herein, and applied to a digital representation of the optical field. Alternatively, the transfer function can be compensated by applying known physical methods, such as in a hologram or spatial light modulator, or in an algorithm, such as in a hill-climbing, simulated annealing or genetic algorithm optimization scheme. As discussed above, once the multimode optical transfer function can be compensated, there are several aspects and methods for obtaining information about the optical properties of the sample or delivering light to the sample. These include adjusting the spatial and other optical properties of proximal light from the transmitter at the input to the multimode waveguide to perform scanning of the focused light into the distal sample. The collected light from the sample could be in a confocal arrangement, or it could be wider area detection from the same or a different wavelength, for example, fluorescence. The collected light can come from a multi-clad or double-clad fiber that allows wide area light collection. Obtaining the optical properties of a sample can take the form of performing optical imaging of the sample's optical properties by collecting the distal light emitted from the sample and correcting for the corruption of the collected light properties as it traverses the multimode optical fiber to the proximal end. Obtaining the optical properties of a sample can also take the form of performing physical or synthetic confocal imaging where focused light is both delivered to and collected from the sample. Obtaining the optical properties of a sample can also take the form of performing dark-field imaging, or similar approaches, where a focused beam is delivered to the sample and higher-order modes are collected and analyzed to determine information about the sample's optical properties. The collected light may be referred to as measurement light.

Figure 7:
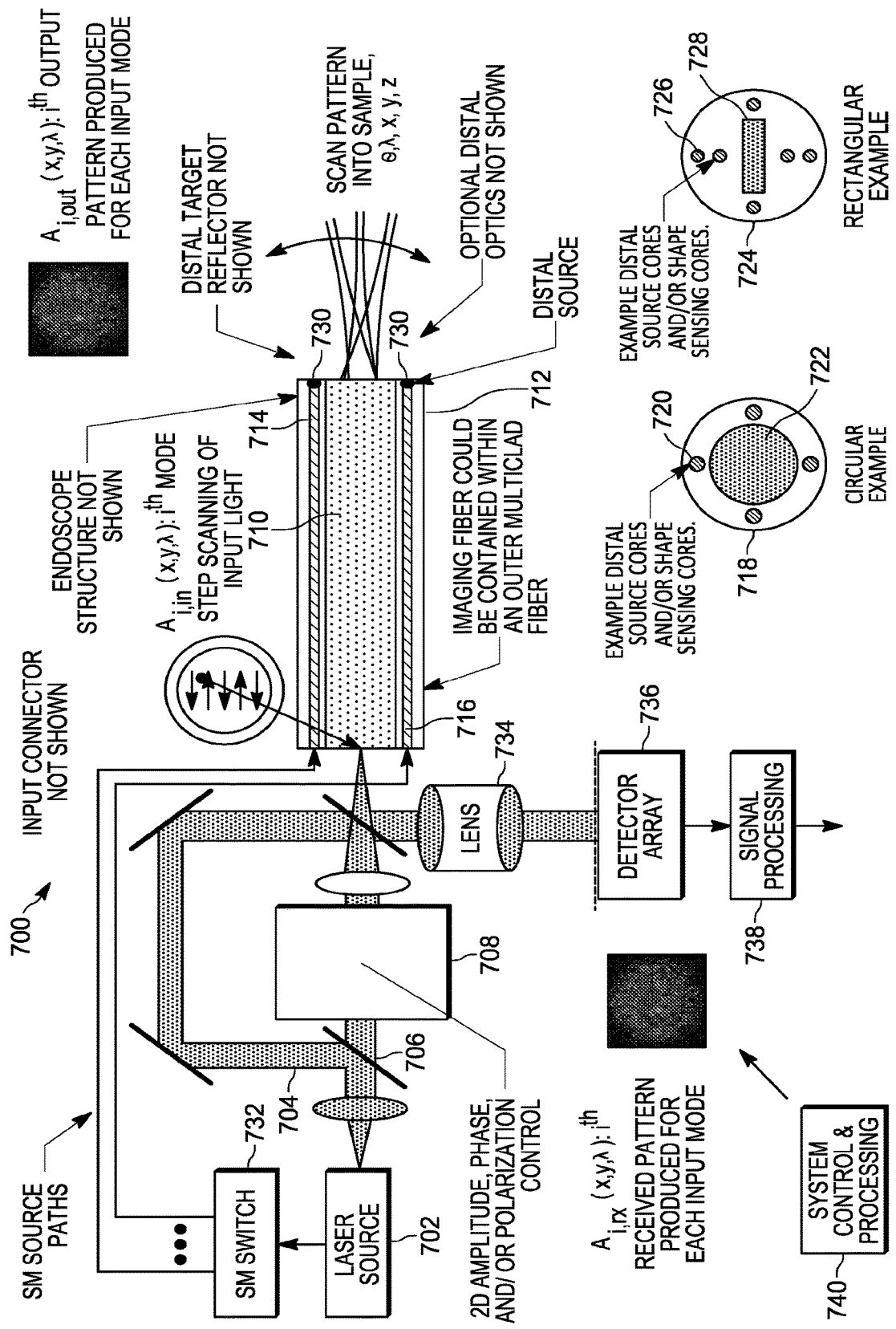
FIG. 7 shows a simplified diagram of an embodiment of a remote optical probe system of the present teaching comprising a single polarization.

FIG. 7 illustrates an embodiment of an optical probe system 700 utilizing coherent detection of the present teaching. The system of FIG. 7 can support either physical scanning/imaging or synthetic scanning/imaging. The remote optical probe system 700 uses a laser (or other optical source) 702. The light from the laser source 702 is split into two paths, a reference path 704, and an illumination path 706. Light in the illumination path 706 passes through a control device 708. The optional control device 708 produces a one or two-dimensional modulation of amplitude and/or phase of the light beam in the illumination path. In some embodiments, a spatial light modulator is used as the control device 708. Optionally, polarization modulation is imparted and/or polarization control is performed in the control device 708. Light from the illumination path illuminates the proximal input facet of a multimode waveguide 710. The multimode waveguide 710 is contained in a multicore fiber 712. The multicore fiber 712 may comprise an outer multi-clad fiber. The input connector that connects the proximal processing system to the multicore fiber 712 is not shown in FIG. 7 nor is the structure of the endoscope that surrounds the multicore fiber 712. The multicore fiber 712 also contains one or more single mode cores 714, 716. One example cross section 718 of the multicore fiber 712 shows how four single mode cores 720 that may be distal source and/or shape sensing cores surround a circular multimode waveguide core 722. A second example cross section 724 of the multicore fiber 712 shows how six single mode cores 726 that may be distal source and/or shape sensing cores surround a rectangular multimode waveguide core 728. One or more distal sources 730 are located at the distal end of the multicore fiber 712. A single mode switch 732 is used to connect light from the laser source 702 to the single mode cores 714, 716 in the multicore fiber 712. The system of FIG. 7 uses the same laser source 702 for imaging in the multimode core as for illuminating the proximally controlled distal sources but alternatively separate light lights could be used. On the receive side of the proximal processing system, an optical element 734 is used to direct light onto a one or two-dimensional coherent detector array 736. The optical element 734 may be one or more lenses. The output of the two-dimensional detector array 736 is connected to signal processing 738 that produces the desired measurement and/or imaging signals. System control and processing 740 is used to control the system so as to perform calibration and measurement collection.

FIG. 7 illustrates the use of coherent detection at the proximal end of the fiber for one polarization. In a first step of one possible method of a calibration sequence for the optical probe system illustrated in FIG. 7, the laser source 702 output from the control device 708 is turned off (or shuttered), and the laser source 702 is turned on along the single mode light paths, labeled SM source paths in FIG. 7, and is connected via the switch 732 to one or several of the single mode fiber cores 714, 716 feeding the distal source 730. Light is back scattered from the distal source 730 and arrives at the 2D coherent detector array 736 and that light distribution is recorded by the system control and processing 740. The received SM light paths can be coherent with the reference path 704 light and can be interferometrically combined on the photodetector. As noted earlier, an optional modular can be added between the laser source 702 and SM switch 732 to impart a modulation to aid in extracting the interference signal. As shown in FIG. 7, the same laser source 702 can be used as the origin of the light that is coupled into the multimode waveguide 710, or it is possible to use two or more different sources for the multimode and single mode cores. Then the SM switch 732 is switched to any remaining SM fibers feeding distal sources and the process is repeated. Alternatively, several or all distal sources can be fed simultaneously. Then the SM source is turned off and the laser source 702 output from the control device 708 is enabled. This 2D field control device 708, which may be a spatial light modulator, is set to generate the first spatial mode and light propagates down the multimode waveguide to a distal target reflector (not shown). The distal target reflector is located at or very near the end of the fiber. Reflected light propagates back down the multimode waveguide 710 to the 2D coherent detector array 736 and is recorded. This process is repeated, with each iteration the control device 708 generates a different linear combination of spatial modes until a sufficient number of linear combinations of spatial modes are recorded. This sufficient number may be equal to the number N of guided modes of the multimode waveguide in Eqs. (1) and (2), or more linear combinations may be used, e.g., to achieve redundancy, or fewer linear combinations may be used, e.g., if one or more of the N modes are not relevant for the imaging accuracy. Although FIG. 7 shows a single polarization embodiment, dual polarization embodiments can be implemented as described in connection with FIG. 4. Thus, there can be optional additional steps for each polarization. Furthermore, there can be additional optional steps for different wavelengths. Using the algorithms described above, the multimode waveguide 710 transfer function can be determined or approximated. At the end of this calibration step, 2D profiles of the amplitude and phase of light from each of the distal sources is recorded as well the two way propagation of light from each of the N input modes. From this, the one-way and two-way optical fiber transfer function can be determined or approximated as described above.

Figure 8:
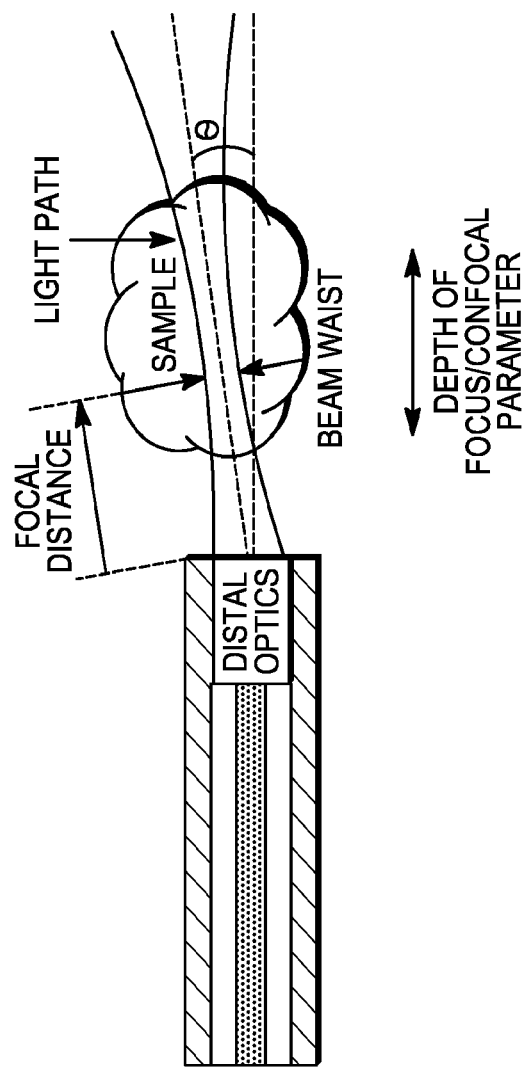
FIG. 8 shows a diagram of the focal distance, beam waist, and depth of focus of an embodiment of a remote optical probe system of the present teaching.

One feature of the remote optical measurement probe of the present teaching is that the output optical field can be physically scanned onto a sample. Once the fiber transfer function is determined or sufficiently well approximated, the desired output pattern of light into the sample can be implemented and adjusted or scanned. In one embodiment, it is desired to scan a near Gaussian-like focused beam, or other desired beam pattern, at the output of the fiber impinging into the sample as shown in FIG. 8. FIG. 8 shows a diagram of the focal distance, beam waist, and depth of focus of an embodiment of a remote optical probe system of the present teaching. Of course many other types of fields (e.g. extended depth-of-field or Bessel beams) can be scanned and the configuration shown in FIG. 8 is just one of many of those examples. Also, it is not always possible to implement a perfect Gaussian beam as only output fields that are a vector sum of fiber Eigenmodes can be reliably implemented. But for a large number N of modes, more complex fields, such as Gaussian or other desired fields, can be closely approximated. The system and multimode transfer function is calibrated fully before an image scan is acquired. In one approach, a shutter in the distal optics blocks light from the sample while the N calibration steps are performed. Then the shutter is opened and the sample is scanned. Alternatively, both reference and sample light may be collected at each of the N steps, with light being distinguished using one of the various forms of gating as described earlier. This has the benefit of increasing the system duty cycle. To achieve the desired light distribution onto the sample, the desired output beam is selected and then transformed mathematically taking into account light propagation (e.g., using Rayleigh-Sommerfeld, Fresnel or Fraunhofer diffraction integrals) between the distal source, the distal tip of the fiber and toward the sample along with the known fiber transfer function. This desired field is implemented at the input facet to the fiber using the amplitude and/or phase control device (e.g. control device 708 of FIG. 7). If the fiber transfer function is continuously measured, both the sample measurement and the fiber transfer function measurement can be done in parallel. Otherwise, the fiber transfer function is measured periodically (intermittently) to calibrate the system as the environmental conditions dictate, and then the sample illumination is performed. Recalibration can be performed when it is determined that the image quality has degraded below some acceptable level. Physical scanning is useful in many applications including confocal imaging, OCT, fluorescence, or multi-photon imaging where high intensity is required in a focal spot.

For OCT and other types of confocal imaging, the light is typically scanned across the sample in a focused optical beam, and backscattered light from the current focal spot is collected. There is a relationship between the complex weighting of the waveguide modes to construct the desired output scan and the weighting that needs to be applied to the modal coefficients that are measured on the proximal end in order to correctly interpret a measurement of the sample and potentially generate an image of the sample (confocal imaging). The equivalent 2D field implemented at the proximal end to achieve a focus a spot within the sample at the distal end, is the same field weights that need to be applied on the collected field that propagates from the sample back to the proximal end. Thus the received sample field on the detector array is processed in a way that is mode-matched to the equivalent field at the input to the optical fiber. Thus light that is backscattered from the sample into the same input mode that was used to achieve a focused spot is the desired light. One skilled in the art will appreciate that one additional feature of this approach using a multimode fiber compared to the traditional single-mode fiber scanning devices shown in FIG. 2 is that it is possible to scan arbitrarily in two dimensions and also that the focal distance can be adjusted to allow 3D imaging and/or implementing complex extended-depth-of-field illumination. Compensating for aberrations in the endoscope housing is also possible. Furthermore, it is possible to collect light in operation modes (not to be confused with waveguide modes) other than the confocal illumination mode, which is something not possible to achieve with a single mode fiber. Changes in cellular structure from things like cancer are known to change the backscattering properties of light and the ability to detect this change electronically by collecting back scattered light from the fundamental mode and other modes can provide useful clinical information.

It is not always necessary to perform confocal or synthetic imaging and sometimes wide-field collection is preferred. In such an embodiment, focused or other desired light pattern is impinging on the sample as described above but there is no need for a 2D detector array in the imaging step (but it is still needed in the calibration step) and all the light reflected into the MM fiber (or even an outer cladding layer or double-cladding fiber) is utilized. This can also be useful in the case of fluorescence imaging, where it is possible to collect the fluorescent light which is emitted at a different wavelength using the same multimode fiber or outer clad fiber. A dichroic or other wavelength selective device directing the light to a large area fluorescent detector could be used at the proximal end Although there is description herein for 2D imaging, it should also be noted that in some embodiments 1D imaging is preferable as shown in the example rectangular fiber geometry of FIG. 7. There would be a corresponding simplification in the spatial light modulator and processing. Such a 1D approach may use some components cylindrical optics to aid in focusing the beam Another aspect of the present teaching is synthetic scanning in a SS-OCT or similar interferometric imaging. Measuring the multimode fiber transfer function requires illuminating N independent modes supported by the fiber. In some embodiment of the present teaching, it is desirable to do this fiber calibration step (perhaps with a shutter closed or simultaneously with some kind of gating) and then do a second step of illuminating or collecting light from the sample. However, in other embodiments, it is possible to do some of these steps simultaneously by extending concepts have been used in synthetic aperture radar, synthetic aperture microscopy, or computational optical interferometry. In these embodiments, the N modes of the fiber are illuminated step-by-step in the calibration procedure but at the same time most of the light is allowed to continue toward the sample. Light from the distal fiber reference target and from the sample are simultaneously collected on the detector array. Using the coherence gating of SS-OCT or other similar approaches, the reflections are separately electronically processed. The calibration procedure is performed as above, and once the fiber transfer function is determined, the desired output scan pattern of light into the sample can also be constructed synthetically, or perhaps numerically is a better word, using a complex weighting of all the input modes to construct the best match to the desired scan pattern in the presence of the multimode fiber transfer function. By knowing the 1-way forward fiber transfer function, one can synthesize the desired output pattern (or a pattern close to it supported by the available fiber modes and inputs) at the distal end. In this arrangement, the sample is illuminated with multiple complex patterns of light and the image is recovered in a manner somewhat analogous to synthetic aperture imaging. Since the multimode endoscope supports N modes, the sample can be illuminated with N synthetic scans. Once the synthesized input light field is known, the detected signal is collected and processed to mathematically determine the back-reflected longitudinal/axial optical profile by doing standard SS-OCT processing. Then 2D and 3D images can be synthesized by varying the desired emission angle to produce images as is known in the art of SS-OCT. Light backscattered into modes other than the illumination mode (e.g. dark-field imaging) can also be analyzed to determine additional optical properties of the sample.

Referring again to FIG. 7, one illustrative example in synthetic scanning is as follows: The first step is the SM sources are activated and the reflected field is collected as noted above. Then, the 2D spatial light modulator is used to impart each of the N modes onto the input facet of the fiber as if to perform the second set of calibration steps as described herein. For example, the 2D spatial light modulator can be replaced by a scanning mirror and then a focused input beam is step scanned over a full raster pattern at the input facet over N orthogonal modes of the multimode fiber (or the fiber input facet could be in a pupil plane). Even if only one mode is coupled into the proximal end of the fiber, it may give rise to a speckle pattern at the distal end of the fiber due to mode coupling. Some light is reflected from the distal reference target and used for calibration as noted above. But also some light is collected from the sample. The two types of light can be numerically separated using time-gating as part the OCT coherence process or other types of temporal or wavelength gating for non-OCT embodiments as known in the art (e.g. separate time-of-flight by if. beat frequency). If the fiber transfer function U is known from the calibration step, and since the input field $A_{i,in}(x,y,\lambda)$ is also known (or measured), then the N speckle patterns be combined synthetically with coefficients $X_i(\theta, \lambda)$ to mathematically yield the desired field scanned across the sample as shown in FIG. 7. That is, $A_{tx,synthetic}(\theta,x,y,\lambda)$ is the sum of $X_i(\theta, \lambda) A_{i,out}(x,y,\lambda)$ which also equals the sum of $X_i(\theta, \lambda) U(x,y,\lambda) A_{i,in}(x,y,\lambda)$. Using this equation $X_i(\theta, \lambda)$ can be determined. The reflected light from each speckle pattern is collected on the detector array for each input focal spot (or input mode if not a focused beam). $A_{i,rx}(x,y,\lambda)$ and confocal detection can be accomplished. Qualitatively, $A_{rx,synthetic}(\theta,x,y,\lambda)$ is the sum of $A_{i,rx}(x,y,\lambda)$ times the vector dot product of the sum of $X_i(\theta, \lambda) A_{i,in}(x,y,\lambda)$. One skilled in the art will appreciate that full traditional SS-OCT is possible but requires large detector bandwidths. It should be noted that coherent but non-OCT embodiments are also possible. In some embodiments where lower bandwidth detectors are desired, a different synthetic scan approach can be used.

FIG. 9A illustrates an embodiment of a remote optical probe system 900 of the present teaching that includes an optical imaging source 902, such as an OCT source or a fixed wavelength laser. A 2D phase and/or polarization control unit 904 processes optical signals from the optical imaging source 902 and direct the processed signal into an endoscope 906. The endoscope 906 includes a multi-core optical fiber 908 and distal optics 910. The output of the 2D phase and/or polarization control unit 904 focuses a spot on the proximal end of the multi-core optical fiber 908. The distal end of the endoscope 906 includes a protective smooth cover 912 suitable for medical use. The resulting physical or synthetic scan pattern is shown illuminating a sample 914.

FIG. 9B-9F illustrates several examples of an imaging fiber with multiple cores. FIG. 9B illustrates a cross section of multiple cores with a common cladding. If the cores are widely spaced, there is little cross coupling and the 2D spatial light modulator (such as control unit 904 of FIG. 9A) can be a simple scanning mirror (or fiber switch) that directs light onto each fiber making the receiver processing very simple. As the cores get closer, coupling occurs and the processing becomes more complex, though the image resolution increases.

FIG. 9C illustrates an embodiment of a remote optical probe system of the present teaching comprising multiple cores each with separate claddings with optional absorptive or light stripping common cladding and/or buffer. This is a multicore fiber with non-common claddings for each core, all embedded in another common cladding. The common cladding can be absorptive or of an index (optionally matched to the buffer) suitable for absorbing or stripping light away from interacting between cores. This approach allows the cores to be more closely packed before significant coupling occurs.

FIG. 9D illustrates an embodiment of a remote optical probe system of the present teaching comprising a hollow core multicore fiber with a coating that minimizes core-to-core coupling. This is a multicore fiber that contains hollow core fibers with a metal or other suitable outer core to confine light into the core. Again the common cladding matrix could be absorbing.

FIG. 9E illustrates an embodiment of a remote optical probe system of the present teaching comprising a multicore optical fiber in combination with a shape sensing fiber. This embodiment illustrates the concept of integrating a multicore fiber with a shape sensing fiber to allow simultaneous imaging and shape sensing.

FIG. 9F illustrates an embodiment of a remote optical probe system of the present teaching comprising a 1D multi-core fiber. This 1D multi-core fiber example could apply to any of the configurations. Optionally, proximal and/or distal masks can be added to minimize or eliminate light not coupled to fiber cores. Also optionally, the distal optics could have a folded mirror and/or have additional mechanical/motor scanning to aid imaging. For example, a folded mirror in combination with an endoscope pull back device could be implemented. One beneficial aspect of these embodiments with minimal core-to-core coupling is some of them can have a very simple system that uses a scanning mirror for a spatial light modulator and simply focuses the light on the fiber input facets. FIG. 9F also shows the optional use of shaping sensing fibers.

Figure 10:
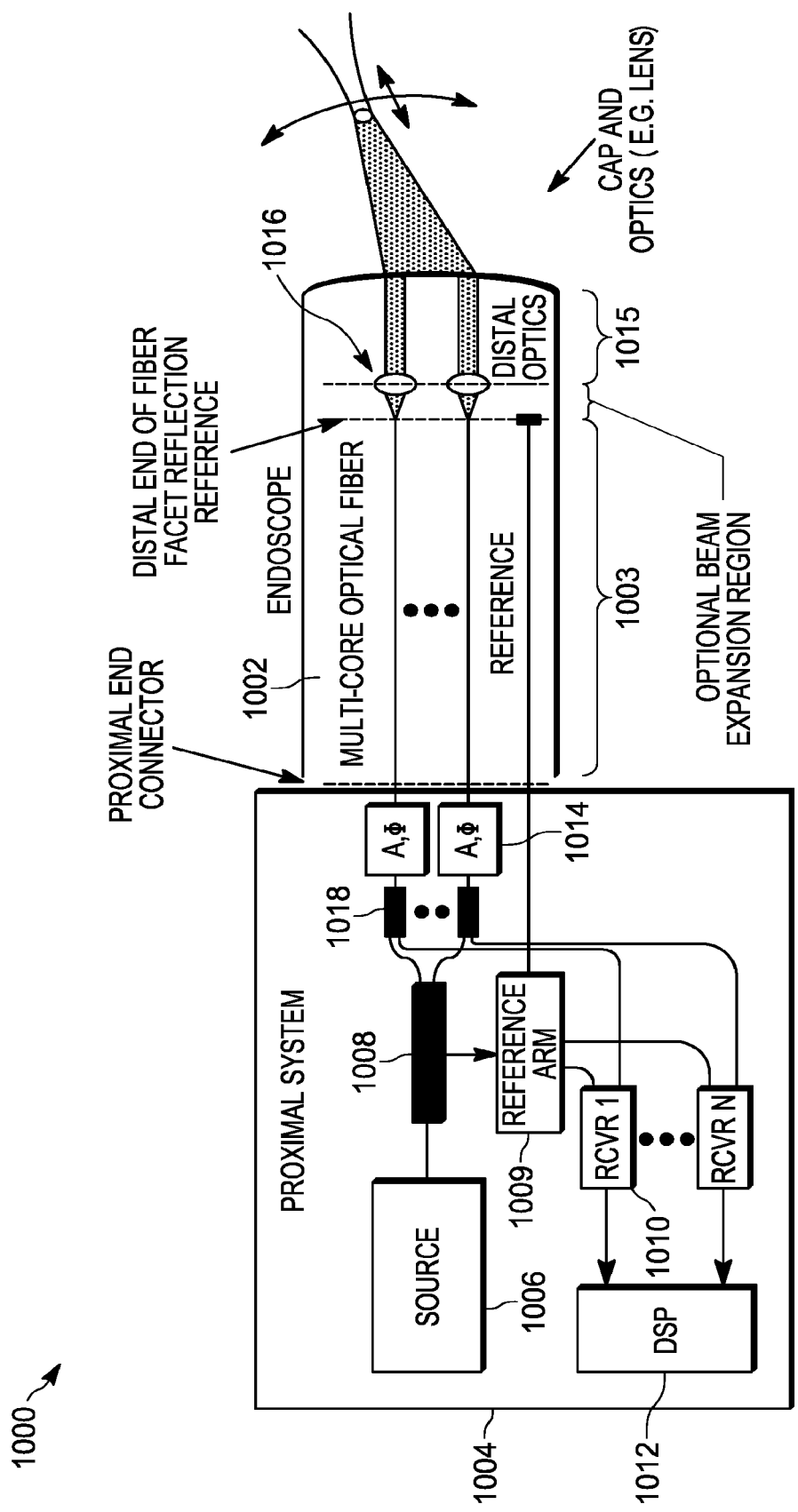
FIG. 10 shows an embodiment of a remote optical probe system of the present teaching comprising a multicore fiber in which each core has a distal reflection and a proximal system that interferometrically collects light from both the distal reflections and the sample and adjusts proximal amplitude and/or phase beam forming elements to perform distal scanning or imaging.

FIG. 10 shows an embodiment of a remote optical probe system 1000 of the present teaching comprising a multicore fiber 1002 in which each core has a distal reflection and a proximal system that interferometrically collects light from both the distal reflections and the sample and adjusts proximal amplitude and/or phase beam forming elements to perform distal scanning or imaging. The multicore fiber 1002 comprises multiple single mode cores acting as waveguides and occupies a portion 1003 of the endoscope. The embodiment is a SS-OCT configuration but other modalities are also possible. The embodiment shown has the multicore fiber 1002 with minimally coupled cores. Each core of the multicore fiber 1002 has a distal reflection and one of the cores is used for a reference arm reflection in analogy with the reference arm of standard SS-OCT. But it is not required that the reference arm be in the same fiber.

A proximal system 1004 is optically coupled to the input of the multicore fiber 1002. The proximal system 1004 comprises an optical source 1006 that generates an optical signal. An optical coupler 1008 separates a portion of the optical signal generated by the optical source 1006 to a reference signal arm 1009. In one embodiment, the reference signal arm 1009 couples the light via the reference core of the multicore fiber to its distal reflection and then back along the same path to a plurality of receivers 1010 that are coupled to a processor 1012 such as DSP processor. Individual amplitude and phase controllers 1014 are then used to form the beam.

At the distal end of the multicore fiber 1002, light from the individual fiber cores is expanded in the optional beam expansion region shown and/or in section 1015 using coreless fiber or one of numerous other beam expanding optical elements. The light can be collimated, focused, or otherwise processed using an optional lens array 1016 that can be implemented using a multicore graded index fiber lens array spliced onto the multicore main fiber. The lens array 1016 allows the output aperture to fill more and operate like a phased array emitter (and collector) vs. widely spaced spatially non-interfering emitters/detectors.

Each fiber in the multicore fiber 1002 has a small distal reference reflection. Thus, at each of the individual receivers 1010 there will be reflected light from the main reference arm 1009 path, light from the individual cores in the multicore fiber reference reflections, and light reflected from the sample. The light propagating back toward the proximal end of the multicore fiber 1002 from the reflectors and/or sample at the distal end are coupled to the receivers 1010 via couplers 1018. The couplers 1018 may also be circulators. The beat signal from the light within the individual cores in the multicore fiber reference reflection and the light from the sample will show up at different i.f. frequencies as is known in the art of SS-OCT. Numerically, in the processing of the proximal system, all the individual multicore fiber reference reflections delays/distances can be determined and whatever desired distal phase and amplitude pattern can be implanted in a closed loop (or open loop) fashion on the field emitted from the multicore fiber and onto the sample. Multiple receivers can be used as shown to perform these functions in parallel. Also, different time delays can be placed in each of the multicore fibers. One receiver can be used with the information showing up as different i.f. frequencies as is known in the art of SS-OCT. This comes at a benefit of increased simplicity but at the cost of reduced SNR due to the N:1 combining loss. It is also possible not to use SS-OCT embodiments but to use other types of interferometric approaches.

Numerous embodiments have been described to make a small imaging endoscope suitable to enable access in hard to reach places in the human body or in other applications. Also as described herein, the present teaching includes the concept of simultaneously using shape sensing fibers to allow both imaging and knowledge of the fibers shape. One additional important aspect for some applications is to enable methods to simultaneously articulate the fiber to allow navigation to remote hard to reach places. There are numerous methods known in the art used in traditional endoscopes to allow navigation through torturous small channels within the human body or in industrial applications outside the human body. But most of these existing techniques require large diameters and complexity.

Figure 11A:
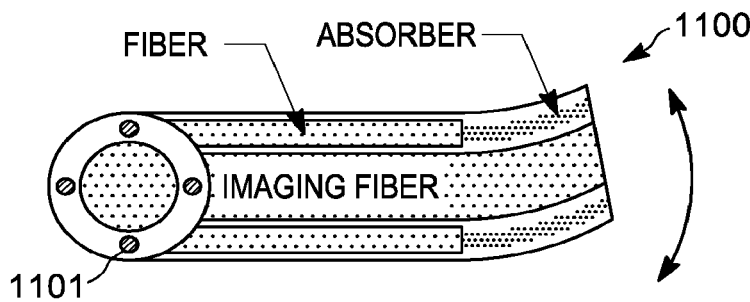
FIG. 11A illustrates an embodiment of a method of the present teaching comprising outer fiber cores having optically absorptive material near the end that is differentially thermally activated, e.g., by a laser, from the proximal end.

FIGS. 11A-E show example methods for articulating a fiber in a small volume. FIG. 11A shows an example of a multicore fiber 1100 where outer optical fibers 1101 are used to deliver laser light to a highly optically absorbing material that induces bending at the distal end of the fiber. Outer fibers 1101 can deliver light for heat induced bending. One skilled in the art will appreciate that cores in a common cladding could be fibers with both cores and claddings embedded in a second common cladding. Additionally, these fibers can be used for shape sensing. The outer fiber has an optically absorptive material near the end of the fiber and is differentially thermally activated by a laser from the proximal end. Alternatively, electrical conductors can be applied to distal thermal expansion material to induce bending.

Figure 11B:
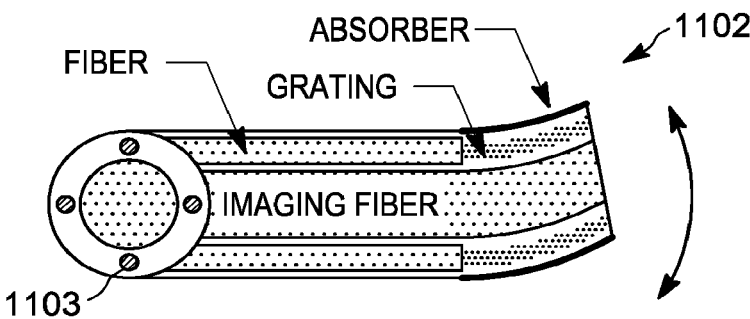
FIG. 11B illustrates an embodiment of a method of the present teaching comprising an outer fiber having fiber Bragg gratings or other structures to reflect light outward to material coated to absorb light and to differential thermally expand.

FIG. 11B shows an alternate example of a multicore fiber 1102 where the thermal/absorbing/bending material is located outside the fibers and fiber Bragg gratings or similar materials are used to reflect light outward toward this absorbing and heat induced bending material. Outer fibers 1103 deliver light for heat induced bending. Additionally, these fibers can be used for shape sensing.

Figure 11C:
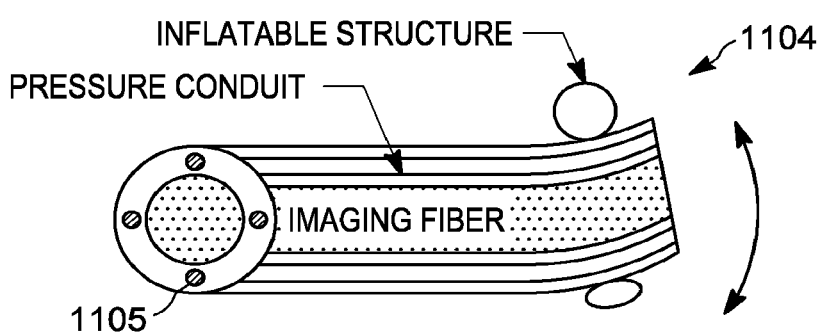
FIG. 11C illustrates an embodiment of a method of the present teaching comprising outer fibers that are hollow and differential liquid, gas, and/or suction pressure is used to bend fiber and/or optional inflatable/deflatable structures are used.

FIG. 11C shows an example of a multicore fiber 1104 with pneumatic induced bending where hollow cores in the fiber, its buffer, or in the jacket are used to induce distal bending. The bending could be due to pressure in the cores. Alternatively, optimally inflatable structures could be added near the end. The outer fibers 1105 are hollow and differential liquid, gas and/or suction pressure may be used to bend the fiber and/or optional inflatable/deflatable structures are used.

Figure 11D:
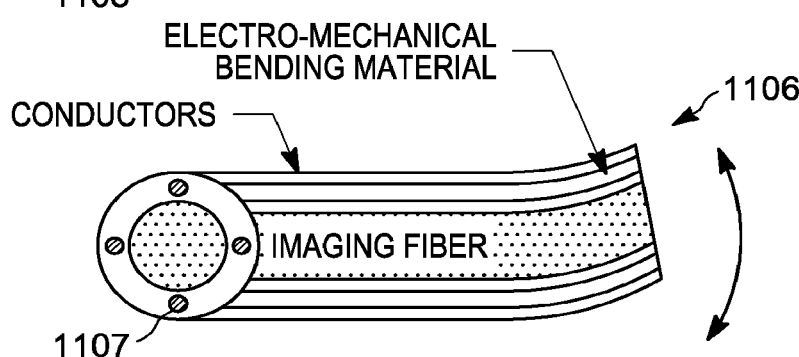
FIG. 11D illustrates an embodiment of a method of the present teaching comprising a distal portion of fiber containing PZT or other electro-mechanical bending material within the fiber cladding, on the jacket/buffer, or around the distal portion of the fiber along with electrical conduits to activate the fiber to bend.

FIG. 11D shows an example of a multicore fiber 1106 where piezoelectric or similar electromechanical material is placed within an outer core of the multicore fiber or its buffer or jacket. Thin electrical wires are used to activate the distal electro-mechanical bending material. If the material is contained within one of the fiber cores, then optionally the preform would be created and the fiber drawn that way. The distal portion of the fiber contains PZT or other electromechanical bending material within the fiber, on the jacket/buffer, or around the distal portion of the fiber along with electrical conduits to activate the fiber to bend. Optional shape sensing fibers 1107 can be used.

Figure 11E:
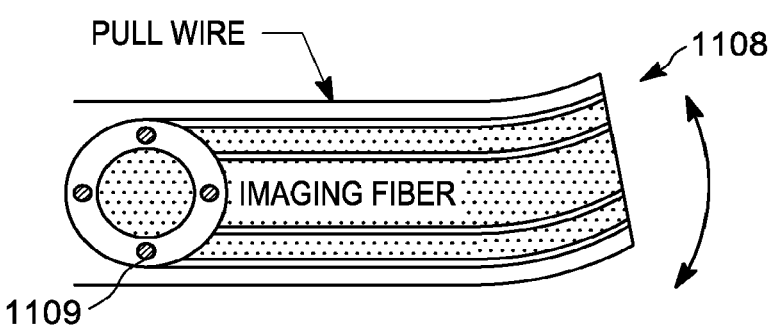
FIG. 11E illustrates an embodiment of a method of the present teaching comprising push/pull wires attached near fiber outer surface.

FIG. 11E shows an example of a multicore fiber 1108 with push/pull wires connected to the distal end of the fiber that are used to articulate bending from a manual system that can include chains and sprockets. Proximal actuation knobs, or motors, or other approaches can be used. Optional shape sensing fibers 1109 can be used.

The multicore fibers illustrated in FIGS. 11 A-E can perform simultaneously imaging and manipulation in a very small volume and optionally to also allow simultaneous shape sensing.

The precise values of $c_s^{(b,L)}$ for distal source may be determined in many ways. FIG. 12 shows a flow chart 1200 for determining the distal source amplitudes $c_s^{(b,L)}$. It also shows how these amplitudes are used in the determination of the imaging fiber transfer matrix. In a preferred embodiment, $c_s^{(b,L)}$ may be determined by performing a single precalibration of the waveguide with access to the distal end before it is used. Such a pre-calibration would be robust to any bends and perturbations to the fiber and would not have to be performed again during use of the imaging waveguide. The pre-calibration would determine the single pass transfer matrix $W^{(b)}$ from the distal to the proximal end, or the single pass transfer matrix $W^{(f)}$ from the proximal to the distal end. The proximal optics would then be turned on to light up the distal source (or sources), and the proximal output $c_s^{(b,0)}$ would be recorded. The single pass precalibration would then be used to determine the distal source amplitudes $c_s^{(b,L)}$ through:

$$c_s^{(b,0)} = W^{(b)} c_s^{(b,L)}$$

It is important to note that the amplitudes $c_s^{(b,L)}$ are independent of any further bends or perturbations on the fiber. The reason for this fact is that the distal source amplitudes are excited from the proximal end by first propagating through a single mode fiber from the proximal to the distal end. Such a single mode path is robust to fiber bends and perturbations. The light from this single mode path then excites the distal source amplitudes $c_s^{(b,L)}$ by coupling to a fixed set of optics, scatterers, and fiber perturbations at the distal end of the fiber. These distal optics are not affected by fiber bends or perturbations.

We note that in order for the single mode waveguide to be truly independent of bends and perturbations it may also be necessary for this waveguide to be single polarization. Thus, the single mode waveguide may be a polarization maintaining waveguide. The single mode waveguide may also be a polarizing waveguide. The single mode waveguide may also be a polarization maintaining optical fiber, a polarization holding optical fiber, or a polarizing single mode optical fiber.

Alternatively, in some configurations according to the present teaching, two polarizations can be launched into the single mode waveguide. The detection at the proximal end of the signal from the distal end may then be performed with polarization diversity detection.

Also, light guided through such a single mode waveguide will accumulate an overall phase that can vary as the fiber is bent or otherwise perturbed. This will add an overall phase to the proximal light distribution, but will not change the spatial pattern. If there is more than one distal source, then such a procedure would be performed with all of the distal sources and an averaging algorithm could be implemented to reduce errors.

More specifically, FIG. 12 illustrates a flow chart 1200 showing an embodiment of imaging waveguide calibration. The flow chart includes steps to be performed before first use 1202 that includes determination of distal source amplitudes. In a first step 1204, the signal pass distal-proximal transfer matrix is determined using distal illumination. In a second step 1206, the distal source is illuminated. In a third step 1208, the proximal E-fields are recorded. In a fourth step 1210, distal E-field amplitudes are computed.

The flow chart 1200 also includes steps 1212 to be performed during use that includes determination of the proximal-distal transfer matrix which is accomplished through a round trip calibration followed by a distal source illumination to remove sign ambiguities in the single pass transfer matrix. In a first step 1214 performed during use, N modes are launched from the proximal side. In a second step 1216, the round trip E fields are recorded. In a third step 1218, the round trip transfer matrix is computed. In a fourth step 1220, the distal source is illuminated. In a fifth step 1222, the proximal E field is recorded. In a sixth step 1224, the ambiguous signs in $W^{(f)}$ are determined.

Figure 13:
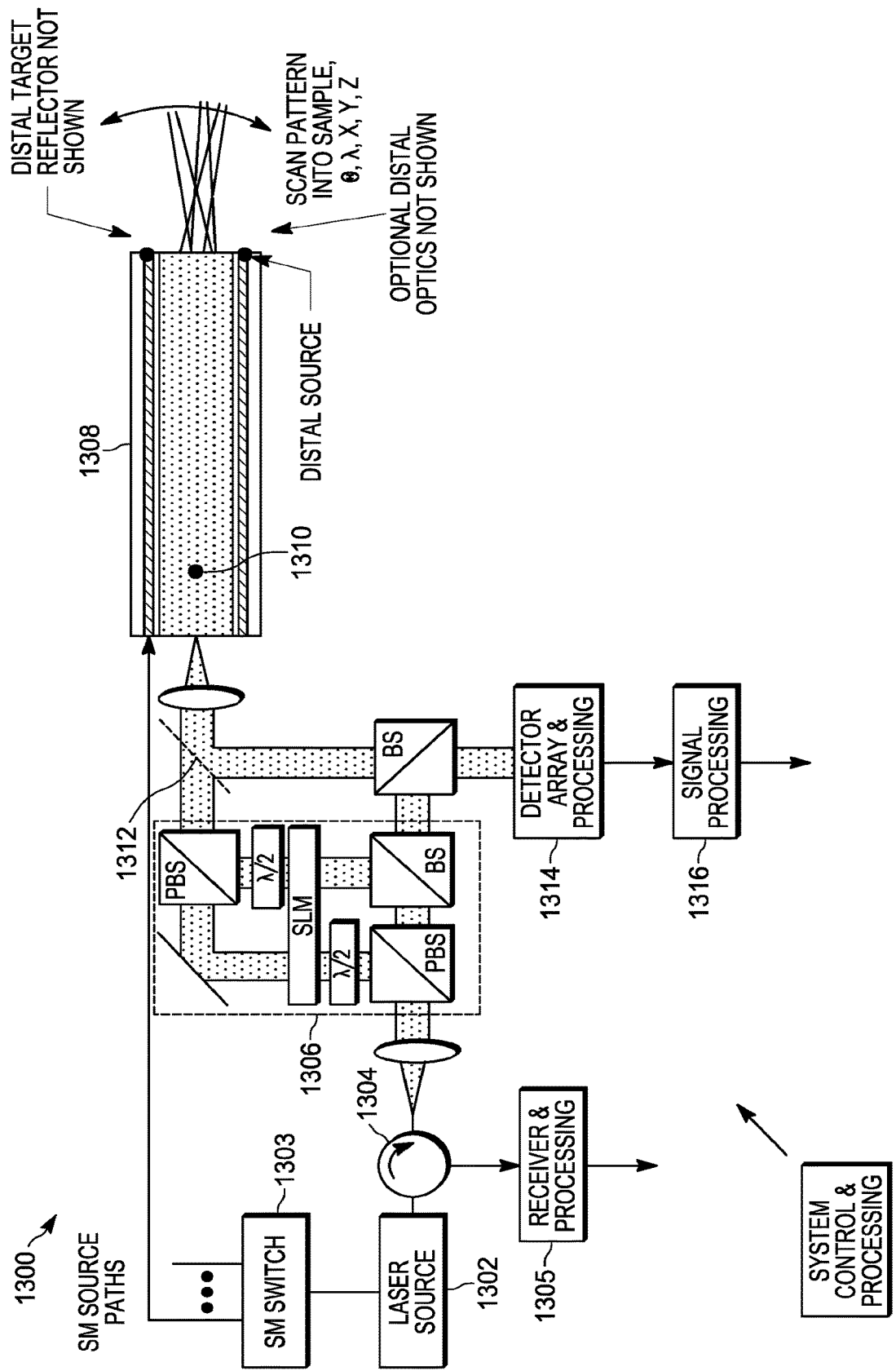
FIG. 13 illustrates an embodiment of an imaging endoscope of the present teaching that uses an architecture with a spatial light modulator and a circulator that is suitable for a confocal, and other, imaging application.

FIG. 13 shows an embodiment of an imaging endoscope 1300 using the multicore and/or multimode fiber according to the present teaching. A laser source (or other type of optical source) 1302 is fiber-coupled to an optical circulator 1304. For example, the laser source 1302 can be coupled using polarization controllers and/or polarization maintaining fiber and optional modulators. The fiber-coupled output of the circulator 1304 is sent into an apparatus 1306 that performs arbitrary spatial/polarization state generation and also to a receiver and processing apparatus 1305. The apparatus 1306 includes polarization beam splitters, mirrors, half wave plates, and optional shutters sandwiched between a spatial light modulator. Numerous types of spatial light modulators can be used. The apparatus 1306 is used to convert the near Gaussian beam from the fiber coupled source 1302 output from circulator 1304 to an arbitrary spatial mode to illuminate the multimode fiber core 1310. Light from the laser source 1302 is also coupled through a single mode switch 1303 directly to the fiber 1308.

The distal sources and other aspects of the fiber and endoscope apparatus 1300 are similar to that described above. Distal optics are not shown at the end of the fiber for simplicity, but it is understood that distal optics will be used in many practical embodiments. Backward propagating light from the reference and/or sample contained in the fiber 1308 is reflected off the beam splitter 1312 and sent onto a coherent detector array 1314 and signal processor 1316 where fiber calibration and other operations can be performed similar to that described above. Note for confocal imaging applications, some of the confocal light will propagate back through the spatial light modulator toward the circulator where it can be separated and sent to a photodetector and receiver processing 1305. This is one of the salient features of this aspect of the invention; namely it allows for relatively simple and fast processing as single channel detector and double passing through the apparatus 1306. Alternatively, two detectors can be used for polarization diversity and/or additional detectors for balanced detection.

In one embodiment of the present teaching, the beam splitter shown as a dotted line can be removed for increased throughput once the fiber is calibrated and a measurement of the optical properties of the sample begins. We also note that there are alternate types of detector array receiver processing that can be used as is known in the art including sequential processing using an arbitrary spatial/polarization state output filter in the reverse direction as a beam analyzer as described in for example, Joel Carpenter, "Everything You Always Wanted to Know About Multimode Fiber", IEEE Photonics Society Newsletter, pp. 4-10, August 2017, which is incorporated herein by reference.

In another aspect of the present teaching, super-resolution imaging of the sample volume can be accomplished by adding an additional phase plate with known properties before the detector. Such a phase plate encodes phase information from the sample and allows imaging with spatial resolution beyond the diffraction limit. See, for example, Bo Shuang, Wenxiao Wang, Hao She, Lawrence J. Tauzin, Charlotte Flateb, Jianbo Chen, Nicholas A. Moring, Logan D. C. Bishop, Kevin F. Kelly & Christy F. Landes, "Generalized Recovery Algorithm for 3D Super-Resolution Microscopy Using Rotating Point Spread Functions", Scientific Reports, 6:30826, DOI: 10.1038/srep30826, 2016, which is incorporated herein by reference. In a confocal arrangement, this allows generation of 3D images.

Another aspect of the present teaching is that, in addition to performing 1D or 2D lateral scanning of a focused light spot on the sample and collecting light reflected or emitted (e.g. fluorescence's) from the sample, it is possible to alter the location of the focus of the light within the sample as well. This is in stark contrast to traditional endoscopes that use single mode fibers where the focus is fixed.

The concept of scanning a focused beam on the sample has been described herein in confocal arrangements, in arrangement suitable for NIR or fluorescence imaging, and other configurations. It should be noted that full-field OCT and other types of full-field imaging are also possible and have advantages in several areas including being less demanding on detector array bandwidth and the ability to acquire data from the sample in parallel.

In yet another embodiment of the present teaching, fields that allow Bessel beam extended depth of focus are implemented. In yet another embodiment of the present teaching, super-resolution imaging is employed.

EQUIVALENTS

While the Applicant's teaching is described in conjunction with various embodiments, it is not intended that the Applicant's teaching be limited to such embodiments. On the contrary, the Applicant's teaching encompasses various alternatives, modifications, and equivalents, as will be appreciated by those of skill in the art, which may be made therein without departing from the spirit and scope of the teaching.

What is claimed is:
1. An optical probe comprising:
 a) a multicore optical fiber having a distal end, a proximal end, a multimode core, and at least one single mode core, the multicore optical fiber configured to propagate light collected from a sample positioned at the distal end of the multicore optical fiber to the proximal end of the multicore fiber; and
 b) a processing system comprising an optical receiver with an input optically coupled to the multicore optical fiber, the optical receiver generating electrical signals corresponding to optical signals received at the input, wherein the processing system compensates for an optical transfer function of the multicore optical fiber using electrical signals generated by the optical receiver such that a corruption of the propagated collected light is corrected, and wherein the optical transfer function is determined by at least two of an initial calibration, a shape measurement of the multicore optical fiber, a temperature measurement, or a strain measurement, and wherein the processing system further produces information about properties of the sample utilizing the optical transfer function.

2. The optical probe of claim 1 wherein the at least one single mode core is configured to perform the shape measurement of the multicore optical fiber.

3. The optical probe of claim 1 wherein the processing system compensates for the optical transfer function of the multicore optical fiber by calculating the optical transfer function.

4. The optical probe of claim 1 wherein the multimode core comprises a few mode optical fiber.

5. The optical probe of claim 1 wherein the information about properties of the sample includes an optical image of the sample using interferometry.

6. The optical probe of claim 1 wherein the information about properties of the sample includes an optical image of the sample using a fluorescence image.

7. The optical probe of claim 1 wherein the information about properties of the sample includes an optical image of the sample using a multi-photon image.

8. The optical probe of claim 1 wherein the information about properties of the sample includes an optical image of the sample using a spectroscopic image.

9. The optical probe of claim 1 wherein the information about properties of the sample includes an optical image of the sample using a reflectance image.

10. The optical probe of claim 1 wherein the multicore optical fiber is configured to provide heat induced bending.

11. The optical probe of claim 1 wherein the multicore optical fiber is configured to provide pneumatic induced bending.

12. The optical probe of claim 1 wherein the multicore optical fiber is configured to provide piezoelectric induced bending.

13. An optical probe comprising:
a) a multicore optical fiber having a distal end, a proximal end, a multimode core, and a single mode core, the multicore optical fiber configured to propagate light collected from a sample positioned at the distal end of the multicore optical fiber to the proximal end of the multicore fiber;
b) a processing system comprising an optical receiver with an input optically coupled to the multicore optical fiber, the optical receiver generating electrical signals corresponding to optical signals received at the input; and
c) an articulation mechanism that provides bending to the multicore optical fiber;
wherein the processing system compensates for an optical transfer function of the multicore optical fiber using electrical signals generated by the optical receiver such that a corruption of the propagated collected light is corrected and produces information about properties of the sample based on the optical transfer function.

14. The optical probe of claim 13 wherein the articulation mechanism provides heat induced bending.

15. An optical probe comprising:
a) a multicore optical fiber having a distal end, a proximal end, a multimode core configured to propagate light collected from a sample positioned at the distal end of the multicore optical fiber, and a plurality of single mode cores configured to obtain a shape measurement of the multicore optical fiber, a temperature measurement of the multicore optical fiber, or a strain measurement of the multicore optical fiber;
b) a processing system comprising an optical receiver with an input optically coupled to the multicore optical fiber, the optical receiver generating electrical signals corresponding to optical signals received at the input, wherein the processing system actively compensates an optical transfer function of the multicore optical fiber, the optical transfer function being determined based on two of more of the following: an initial calibration, the shape measurement of the multicore optical fiber, the temperature measurement of the multicore optical fiber, or the strain measurement of the multicore optical fiber, and produces information about properties an optical image of the sample.

16. An optical probe comprising:
a) an optical source that generates light;
b) a multicore optical fiber comprising a multimode core and a plurality of single mode cores, the multicore optical fiber having a proximal end with an input optically coupled to the optical source and configured to deliver the generated light to a sample positioned distal to a distal end of the multicore optical fiber;
c) an optical receiver having an input optically coupled to the multicore optical fiber, the optical receiver configured to receive light that is propagated from the distal end to the proximal end of the multicore optical fiber; and
d) a processor electrically coupled to the optical receiver and the optical source, the processor configured to control the optical source such that the generated light is transmitted to the sample, the processor further configured to compensate for an optical transfer function of the multicore optical fiber utilizing two or more of the following: an initial calibration, a shape measurement of the multicore optical fiber, a temperature measurement of the multicore optical fiber, or a strain measurement of the multicore optical fiber, and the processor further configured to produce information about properties of the sample based on the received light that is propagated from the distal end to the proximal end of the multicore optical fiber.

17. The optical probe of claim 16 wherein at least one of the plurality of single mode cores is configured for shape sensing and comprises a distal optical source.

18. An imaging probe comprising:
a) an optical source that generates light at an output;
b) a multicore optical fiber comprising a multimode core and a single mode core, the multicore optical fiber having a proximal end with an input optically coupled to the optical source and configured to deliver the generated light to a sample positioned at a distal end of the multicore optical fiber;
c) an articulation mechanism that provides bending to the multicore optical fiber;
d) an optical receiver having an input optically coupled to the multicore optical fiber, the optical receiver configured to receive light that is propagated from the distal end to the proximal end of the multicore optical fiber; and e) a processor electrically coupled to the optical receiver and the optical source, the processor configured to:
  i) control the optical source such that the generated light delivered to the sample is scanned across the sample,
  ii) compensate for a transfer function of the multicore optical fiber, and
  iii) produce an image of the sample based on the received light that is propagated from the distal end to the proximal end of the multicore optical fiber.

19. The imaging probe of claim 18 wherein the articulation mechanism comprises at least one of thermal, optical, electro-mechanical, inflatable, or pull-wire articulation mechanism.

20. The optical probe of claim 18 wherein the single mode core performs shape sensing and provides a distal optical source.

* * * * *